(12) United States Patent
Akikaze et al.

(10) Patent No.: US 9,072,983 B2
(45) Date of Patent: Jul. 7, 2015

(54) VINYL SULFONIC ACID, POLYMER THEREOF, AND PRODUCTION METHOD THEREOF

(75) Inventors: Hiroshi Akikaze, Osaka (JP); Takehiko Miyai, Nobeoka (JP); Kazuhiko Isshiki, Osaka (JP)

(73) Assignee: Asahi Kasei Finechem Co., Ltd., Osaka (JP)

( * ) Notice: Subject to any disclaimer, the term of this patent is extended or adjusted under 35 U.S.C. 154(b) by 1083 days.

(21) Appl. No.: 12/933,964

(22) PCT Filed: Mar. 27, 2009

(86) PCT No.: PCT/JP2009/056286
§ 371 (c)(1),
(2), (4) Date: Sep. 22, 2010

(87) PCT Pub. No.: WO2009/119806
PCT Pub. Date: Oct. 1, 2009

(65) Prior Publication Data
US 2011/0017954 A1    Jan. 27, 2011

(30) Foreign Application Priority Data

| | | |
|---|---|---|
| Mar. 28, 2008 | (JP) | 2008-085670 |
| Mar. 28, 2008 | (JP) | 2008-085693 |
| May 30, 2008 | (JP) | 2008-143072 |
| May 30, 2008 | (JP) | 2008-143400 |
| Jun. 26, 2008 | (JP) | 2008-167810 |

(51) Int. Cl.
*H01B 1/12* (2006.01)
*B01D 1/06* (2006.01)
*B01D 3/02* (2006.01)
*C07C 309/20* (2006.01)
*C08F 220/44* (2006.01)
*C08F 228/02* (2006.01)
*H01M 8/10* (2006.01)

(52) U.S. Cl.
CPC *B01D 1/065* (2013.01); *B01D 3/02* (2013.01); *C07C 309/20* (2013.01); *C08F 220/44* (2013.01); *C08F 228/02* (2013.01); *H01M 8/1023* (2013.01); *H01M 8/1025* (2013.01); *H01M 8/103* (2013.01); *H01M 8/1044* (2013.01); *H01M 8/1072* (2013.01); *Y02E 60/521* (2013.01)

(58) Field of Classification Search
None
See application file for complete search history.

(56) References Cited

U.S. PATENT DOCUMENTS

| | | | |
|---|---|---|---|
| 2,597,696 A | 5/1952 | Anthes et al. | |
| 2,619,452 A * | 11/1952 | Jones et al. | 203/4 |
| 3,312,735 A * | 4/1967 | Medford et al. | 562/124 |
| 6,180,320 B1 | 1/2001 | Saito et al. | |
| 6,340,414 B1 | 1/2002 | Hommeltoft | |
| 8,299,294 B2 * | 10/2012 | Akikaze et al. | 562/124 |
| 2003/0008504 A1 | 1/2003 | Miyazaki | |
| 2003/0166381 A1 | 9/2003 | Lee et al. | |
| 2004/0092700 A1 | 5/2004 | Hsu | |
| 2006/0223008 A1 | 10/2006 | Yoshimura et al. | |
| 2007/0193686 A1 | 8/2007 | Miyazaki et al. | |
| 2009/0029168 A1 | 1/2009 | Butters et al. | |
| 2009/0030149 A1 | 1/2009 | Morita et al. | |
| 2009/0297909 A1 | 12/2009 | Yamamoto et al. | |
| 2010/0081840 A1 | 4/2010 | Akikaze et al. | |

FOREIGN PATENT DOCUMENTS

| | | |
|---|---|---|
| JP | 04-275270 A | 9/1992 |
| JP | 06-329615 A | 11/1994 |
| JP | 07-138224 A | 5/1995 |
| JP | 08-206482 A | 8/1996 |
| JP | 08-325598 A | 12/1996 |
| JP | 09-012531 | 1/1997 |
| JP | 09-512532 A | 12/1997 |
| JP | 10-120968 | 5/1998 |
| JP | 2000-35672 | 2/2000 |
| JP | 2000-053629 A | 2/2000 |
| JP | 2000-191629 A | 7/2000 |
| JP | 2000-195489 | 7/2000 |
| JP | 2001-250807 | 9/2001 |
| JP | 2002-035607 A | 2/2002 |
| JP | 2003-031198 | 1/2003 |
| JP | 2003-137858 A | 5/2003 |
| JP | 2003-155261 A | 5/2003 |
| JP | 2004-31905 | 1/2004 |
| JP | 2004-149569 A | 5/2004 |

(Continued)

OTHER PUBLICATIONS

Kunichika et al., Bulletin of the Institute for Chemical Research, Kyoto University (1961), 39(3): 215-225.*

(Continued)

*Primary Examiner* — Karl J Puttlitz

(74) *Attorney, Agent, or Firm* — Morgan, Lewis & Bockius LLP

(57) ABSTRACT

(1) A vinyl sulfonic acid, having a double bond content of 95 wt. % or more, and (i) a sodium (Na) content of 1 ppm or less, and (ii) a content of at least one metal selected from the group consisting of alkali earth metal and first row transition metal of 1 ppm or less. Alternatively, (2) a vinyl sulfonic acid, having a double bond content of 95 wt. % or more, and (i) a sodium (Na) content of 100 ppb or less, and (ii) a content of at least one metal selected from the group consisting of alkali earth metal and first row transition metal of 100 ppb or less. Further, a homopolymer or copolymer thereof, a production method thereof, or a thin-film distillation apparatus suited for the production thereof.

17 Claims, 2 Drawing Sheets

(56) References Cited

FOREIGN PATENT DOCUMENTS

| | | |
|---|---|---|
| JP | 2004-189820 | 7/2004 |
| JP | 2005-536595 | 2/2005 |
| JP | 2005-190940 | 7/2005 |
| JP | 2006-179678 | 7/2006 |
| JP | 2006-259382 | 9/2006 |
| JP | 2007-150153 | 6/2007 |
| JP | 4048063 B | 11/2007 |
| JP | 2008-063567 A | 3/2008 |
| JP | 2008-536971 A | 9/2008 |
| WO | WO2006059582 | 6/2006 |
| WO | 2007/058036 A | 5/2007 |
| WO | WO2008078767 | 7/2008 |

OTHER PUBLICATIONS

Extended European Search Report issued in corresponding European Patent Application No. 09726253.9 dated Oct. 31, 2012.
Preston et al., "5. A Convenient Preparation for Ethylenesulfonic Acid," Journal of Polymer Science, 2: 5364-5365 (1969).
Krell et al., "Separating processes," Handbook of Laboratory Distillation, Elsevier, 203-306 (1982).
Breslow et al., "Ethylenesulfonic acid polymers," Encyclopedia of Polymer Science and Engineering, 6: 564-570 (1986).
Office Action issued in related Japanese Patent Application No. 2009-285273 dated Nov. 22, 2013.
Laconti et al., Mechanisms of membrane degradation, Chapter 49, Fuel Cell Technology and Applications, vol. 3, Handbook of Fuel Cells, pp. 647-662, 2003.
Kunichika et al., Journal of the Chemical Society of Japan, Industrial Section vol. 64, No. 5, pp. 929-932, 1961.
Chemical Apparatus Handbook, edited byt the Society for Chemical Engineers, Japan, published by Maruzen, pp. 499-500, 1970.
Polymer Handbook, Fourth Edition, Published by John Wiley & Sons Inc., pp. II/318-II/319, 2003.

* cited by examiner

VINYL SULFONIC ACID, POLYMER THEREOF, AND PRODUCTION METHOD THEREOF

CROSS-REFERENCE TO RELATED APPLICATIONS

The present application is a U.S. National Phase Application of International Application PCT/JP2009/056286 filed Mar. 27, 2009, which claims the benefit of Japanese Patent Application Nos. 2008-085670, filed Mar. 28, 2008, 2008-085693, filed Mar. 28, 2008, 2008-143072, filed May 30, 2008, 2008-143400, filed May 30, 2008, and 2008-167810, filed Jun. 26, 2008, which are hereby incorporated by reference in their entirety.

TECHNICAL FIELD

The present invention mainly relates to a vinyl sulfonic acid, a polymer thereof, a production method thereof, an apparatus suitable for production thereof, and an electric/electronic material comprising the vinyl sulfonic acid or polymer thereof.

BACKGROUND ART

Vinyl sulfonic acids are attracting a great deal of attention as a monomer for constituting a functional polymer and a conductive material.

However, commercially available vinyl sulfonic acids have a double bond content of 75 wt. % or less. Consequently, when the vinyl sulfonic acid was to be polymerized after impregnating in a porous substrate, polymerization did not proceed sufficiently and thus a product functioning as a proton conductive polymer could not be obtained.

Patent Document 1 describes a vinyl sulfonic acid with a purity of 98%. However, the metal content is several ppm.

Recently, vinyl sulfonic acids or polymers thereof are attracting attention as a component constituting functional polymers and conductive materials, and as a material for electronic devices and semiconductors.

For example, a vinyl sulfonic acid or polymer thereof has been reported as being utilized in a resist resin composition (Patent Document 2), a resin composition for a resist protection film (Patent Documents 3 and 4), a CMP slurry (Patent Documents 5 and 6), a separator for an alkali secondary battery (Patent Documents 7 and 8), a fuel cell electrolyte membrane (Patent Documents 1 and 9), a conductive polymer dopant (Patent Documents 10 and 11) and the like.
Patent Document 1: WO 2006/059582
Patent Document 2: Japanese Patent Laid-Open No. 2000-035672
Patent Document 3: Japanese Patent Laid-Open No. 10-120968
Patent Document 4: Japanese Patent Laid-Open No. 2006-259382
Patent Document 5: Japanese Patent Laid-Open No. 2004
Patent Document 6: Japanese Patent Laid-Open No. 2006-179678
Patent Document 7: Japanese Patent Laid-Open No. 2000-195489
Patent Document 8: Japanese Patent Laid-Open No. 2003-031198
Patent Document 9: Japanese Patent No. 4048063
Patent Document 10: National Publication of International Patent Application No. 2005-536595
Patent Document 11: Japanese Patent Laid-Open No. 2005-190940

However, many of these uses dislike metal or impurity contamination.

For example, for a semiconductor material, impurities, especially metal impurities contained in the material, can cause problems such as contamination of the wafer by diffusing into the wafer interior during the wafer fabrication step. Further, metal contamination can induce deteriorated reliability of the dielectric film, current leakage, and abnormalities in film deposition and the like, and also have an substantial adverse impact on the semiconductor apparatus (see Patent Documents 12 to 14).
Patent Document 12: Japanese Patent Laid-Open No. 2007-150153
Patent Document 13: Japanese Patent Laid-Open No. 2004-189820
Patent Document 14: Japanese Patent Laid-Open No. 2001-250807

Further, recently, from the perspectives that solid polymer fuel cells utilizing a polymer electrolyte membrane have a light burden on the environment and reduced carbon dioxide emissions, investigations are being carried out on their various applications, such as for automobiles and fixed household use.

Conventionally, a perfluoroalkyl sulfonate-type polymer in which sulfonic acid groups are linked to side chains on a perfluoro skeleton has been used as such a polymer electrolyte membrane. Further, perfluoroalkyl sulfonate-type polymers which have undergone various improvements have been developed. However, since the polymer production process is complex, and a fluorinated hydrocarbon-based material, for which large cost reductions are not easy to achieve, is used, costs increase.

Accordingly, hydrocarbon-based polymer electrolyte membranes which do not use a fluorine-based polymer and which have improved proton conductivity have been developed. Hydrocarbon-based polymer electrolyte membranes are easy to produce, can be applied in a large variety of molecular structures, and have easily-controlled physical properties. Further, from a recycling perspective, since hydrocarbon-based polymer electrolyte membranes do not contain a fluorine, they have the advantage of not producing harmful substances.

However, hydrocarbon-based polymers have worse chemical stability than perfluoroalkyl sulfonate-type polymers. This is due to the fact that hydrogen and oxygen crossleak across the electrolyte membrane and react on the electrode catalyst to produce hydrogen peroxide, whereby radicals produced from this hydrogen peroxide cause the membrane to deteriorate. Further, iron ions act as a catalyst for promoting the oxidation ability of the hydrogen peroxide, so that the membrane deterioration is accelerated (see Non-Patent Document 1).
Non-Patent Document 1: Fuel Cell Technology and Applications/Handbook of Fuel Cells, pp. 647-662, 2003

However, a vinyl sulfonic acid or polymer thereof having a sufficiently reduced metal content is as yet unknown.

On the other hand, various methods are known for producing a vinyl sulfonic acid (see Non-Patent Document 2). For example, Patent Document 15 describes a method for producing a vinyl sulfonic acid by performing a sodium removal treatment on sodium vinyl sulfonate with hydrochloric acid.

Further, Patent Document 16 describes a method for producing a vinyl sulfonic acid by dehydrating isethionic acid using diphosphate pentoxide or pyrophosphoric acid as a dehydrating agent.

However, in the above-described methods, a product having sufficient quality cannot be obtained.

Non-Patent Document 2: Sango Kunichika, Takao Katagiri, Journal of the Chemical Society of Japan, Industrial chemistry section Vol. 64, No. 5, 1961, pp. 929-932

Patent Document 15: U.S. Pat. No. 3,312,735

Patent Document 16: U.S. Pat. No. 2,597,696

DISCLOSURE OF THE INVENTION

Problems to be Solved by the Invention

It is the main object of the present invention to provide a vinyl sulfonic acid having a high double bond content and a low metal content. Further, it is an object of the present invention to provide a homopolymer and a copolymer comprising this vinyl sulfonic acid as a constituent component, and a production method thereof. In addition, it is an object of the present invention to provide an electric/electronic material comprising this vinyl sulfonic acid or a polymer thereof. Still further, it is an object of the present invention to provide an apparatus or a method suitable for the production of the above vinyl sulfonic acid.

Means for Solving the Problems

Mainly for the purpose of resolving the above-described problems, and as a result of extensive investigations, the present invention discovered that a vinyl sulfonic acid having excellent qualities could be obtained, and as a result of further extensive investigations, completed the present invention.

Specifically, the present invention provides the following vinyl sulfonic acids, homopolymers, copolymers, production methods, apparatuses, and electric/electronic materials.

Item 1. A vinyl sulfonic acid characterized by having:
 a double bond content of 95 wt. % or more; and
 (i) a sodium (Na) content of 1 ppm or less; and
 (ii) a content of at least one metal selected from the group consisting of alkali earth metal and first row transition metal of 1 ppm or less.

Item 1-1. The vinyl sulfonic acid according to item 1, which is obtained by subjecting a vinyl sulfonate to a metal removal treatment so that a metal removal rate represented by the following formula is 95% or more:

Metal removal rate(%)={(acid value after metal removal treatment)/(acid value before metal removal treatment)}×100.

Item 1-2. The vinyl sulfonic acid according to item 1, which is obtained by subjecting a vinyl sulfonate to a metal removal treatment with a strongly-acidic ion-exchange resin.

Preferably, the vinyl sulfonic acid according to item 1-2, wherein the metal removal treatment is a treatment in which a metal removal rate represented by the following formula is 95% or more:

Metal removal rate(%)={(acid value after metal removal treatment)/(acid value before metal removal treatment)}×100.

Item 1-3. The vinyl sulfonic acid according to item 1-1 or 1-2, obtained by purifying the product obtained from the metal removal treatment by further subjecting such product to thin-film distillation.

Item 2. A vinyl sulfonic acid characterized by having:
 a double bond content of 95 wt. % or more; and
 (i) a sodium (Na) content of 100 ppb or less; and
 (ii) a content of at least one metal selected from the group consisting of alkali earth metal and first row transition metal of 100 ppb or less.

Item 2-1. The vinyl sulfonic acid according to item 2, which is obtained by subjecting a vinyl sulfonate to a metal removal treatment so that a metal removal rate represented by the following formula is 95% or more:

Metal removal rate(%)={(acid value after metal removal treatment)/(acid value before metal removal treatment)}×100.

Item 2-2. The vinyl sulfonic acid according to item 2, which is obtained by subjecting a vinyl sulfonate to a metal removal treatment with a strongly-acidic ion-exchange resin.

Preferably, the vinyl sulfonic acid according to item 2-2, wherein the metal removal treatment is a treatment in which a metal removal rate represented by the following formula is 95% or more:

Metal removal rate(%)={(acid value after metal removal treatment)/(acid value before metal removal treatment)}×100.

Item 2-3. The vinyl sulfonic acid according to item 2-1 or 2-2, obtained by purifying the product obtained from the metal removal treatment by further subjecting such product to thin-film distillation.

Item 2-4. The vinyl sulfonic acid according to item 2, obtainable (obtained) by subjecting a vinyl sulfonate to a metal removal treatment in which a metal removal rate represented by the following formula is 95% or more:

Metal removal rate(%)={(acid value after metal removal treatment)/(acid value before metal removal treatment)}×100, and purifying the product obtained from the metal removal treatment using:
(1) a thin-film distillation apparatus wherein all or a part of a contact with the vinyl sulfonic acid or a composition thereof is formed from tantalum, or
(2) the thin-film distillation apparatus according to the above (1), comprising:
 a distillation tower for evaporating a distillation raw material;
 a vinyl sulfonic acid vapor outlet which is provided in a middle section of the distillation tower; and
 a cooling device, which is arranged externally to the distillation tower, for condensing the vinyl sulfonic acid vapor obtained from the outlet, and preferably, the thin-film distillation apparatus according to the above (1), comprising a distillation tower for evaporating the vinyl sulfonic acid which has been subjected to the metal removal treatment, a vinyl sulfonic acid vapor outlet which is provided in a middle section of the distillation tower, and a cooling device, which is arranged externally to the distillation tower, for condensing the vinyl sulfonic acid vapor obtained from the outlet.

Item 2-5. The vinyl sulfonic acid according to item 2, obtainable (obtained) by subjecting a vinyl sulfonate to a metal removal treatment by bringing the vinyl sulfonate into contact with a strongly-acidic ion-exchange resin, and purifying the product obtained from the metal removal treatment using:
(1) a thin-film distillation apparatus wherein all or a part of a contact with the vinyl sulfonic acid or a composition thereof are formed from tantalum, or (2) the thin-film distillation apparatus according to the above (1), comprising:
    a distillation tower for evaporating a distillation raw material;
    a vinyl sulfonic acid vapor outlet which is provided in a middle section of the distillation tower; and
    a cooling device, which is arranged externally to the distillation tower, for condensing the vinyl sulfonic acid vapor obtained from the outlet, and preferably, the thin-film distillation apparatus according to the above (1), comprising a distillation tower for evaporating the vinyl sulfonic acid which has been subjected to the metal removal treatment, a vinyl sulfonic acid vapor outlet which is provided in a middle section of the distillation tower, and a cooling device, which is arranged externally to the distillation tower, for condensing the vinyl sulfonic acid vapor obtained from the outlet.

Item A: A raw material for an electric/electronic material comprising the vinyl sulfonic acid according to item 1 or 2. Alternatively, use of the vinyl sulfonic acid according to item 1 or 2 in order to produce an electric/electronic material.

Item 3. A vinyl sulfonic acid homopolymer or copolymer obtained by polymerizing the vinyl sulfonic acid according to item 1 or 2 alone or with one or more other monomers copolymerizable therewith.

Item 3-1. A vinyl sulfonic acid homopolymer comprising the vinyl sulfonic acid according to any of items 1 to 1-3 as a monomer, or a vinyl sulfonic acid homopolymer comprising the vinyl sulfonic acid according to any of items 2 to 2-5 as a monomer.

Item 3-2. A vinyl sulfonic acid copolymer obtained by polymerizing the vinyl sulfonic acid according to any of items 1 to 1-3 with one or more other monomers copolymerizable therewith, or a vinyl sulfonic acid copolymer obtained by polymerizing the vinyl sulfonic acid according to any of items 2 to 2-5 with one or more other monomers copolymerizable therewith.

Item B. A raw material for an electric/electronic material comprising the vinyl sulfonic acid homopolymer or copolymer according to item 3, 3-1, or 3-2. Alternatively, use of the vinyl sulfonic acid homopolymer or copolymer according to item 3, 3-1, or 3-2 in order to produce an electric/electronic material.

Item 4. A method for producing a vinyl sulfonic acid homopolymer or copolymer, comprising a step of subjecting the vinyl sulfonic acid according to item 1 or 2 alone or with one or more other monomers copolymerizable therewith to radical polymerization, photopolymerization, or radiation polymerization.

Item 4-1. A method for producing a vinyl sulfonic acid homopolymer, characterized by subjecting the vinyl sulfonic acid according to any of items 1 to 1-3 to radical polymerization, photopolymerization, or radiation polymerization, or a method for producing a vinyl sulfonic acid homopolymer, characterized by subjecting the vinyl sulfonic acid according to any of items 2 to 2-5 to radical polymerization, photopolymerization, or radiation polymerization.

Item 4-2. A method for producing a vinyl sulfonic acid copolymer, comprising subjecting the vinyl sulfonic acid according to any of items 1 to 1-3 to radical polymerization, photopolymerization, or radiation polymerization with one or more other monomers copolymerizable therewith, or a method for producing a vinyl sulfonic acid copolymer, comprising subjecting the vinyl sulfonic acid according to any of items 2 to 2-5 to radical polymerization, photopolymerization, or radiation polymerization with one or more other monomers copolymerizable therewith.

Item 5. A thin-film distillation apparatus for vinyl sulfonic acid purification, wherein all or a part of a contact with a vinyl sulfonic acid or a composition thereof are formed from a material having a high corrosion resistance.

Especially, a thin-film distillation apparatus for vinyl sulfonic acid purification, characterized in that all or a part of a contact with a vinyl sulfonic acid or a composition thereof are formed from tantalum.

Item 6. The thin-film distillation apparatus according to item 5, comprising:
    a distillation tower for evaporating a distillation raw material;
    a vinyl sulfonic acid vapor outlet which is provided in a middle section of the distillation tower; and
    a cooling device which is arranged externally to the distillation tower for condensing the vinyl sulfonic acid vapor obtained from the outlet.

Especially, the thin-film distillation apparatus according to item 5, comprising:
    a distillation tower for evaporating a vinyl sulfonic acid which has been subjected to a metal removal treatment;
    a vinyl sulfonic acid vapor outlet which is provided in a middle section of the distillation tower; and
    a cooling device which is arranged externally to the distillation tower for condensing the vinyl sulfonic acid vapor obtained from the outlet.

Item 7. A method for producing the vinyl sulfonic acid according to item 1 or 2, characterized by comprising:
    a step of subjecting a vinyl sulfonate to a metal removal treatment; and
    a step of purifying the product obtained from the metal removal treatment using the thin-film distillation apparatus according to item 5 or 6.

Item C. The vinyl sulfonic acid according to item 1 or 2, obtainable (obtained) by subjecting a vinyl sulfonate to a metal removal treatment in which a metal removal rate represented by the following formula is 95% or more, $$\text{Metal removal rate}(\%)=\{(\text{acid value after metal removal treatment})/(\text{acid value before metal removal treatment})\}\times 100\text{, and}$$

purifying the product obtained from the metal removal treatment using the thin-film distillation apparatus according to item 5 or 6.

Especially, the vinyl sulfonic acid according to item 2, obtainable (obtained) by subjecting a vinyl sulfonate to a metal removal treatment in which a metal removal rate represented by the following formula is 95% or more:

$$\text{Metal removal rate}(\%)=\{(\text{acid value after metal removal treatment})/(\text{acid value before metal removal treatment})\}\times 100\text{, and}$$

purifying the product obtained from the metal removal treatment using the thin-film distillation apparatus according to item 6.

Item D. The vinyl sulfonic acid according to item 1 or 2, obtainable (obtained) by subjecting a vinyl sulfonate to a metal removal treatment by bringing the vinyl sulfonate into contact with a strongly-acidic ion-exchange resin, and purifying the product obtained from the metal removal treatment using the thin-film distillation apparatus according to item 5 or 6.

Especially, the vinyl sulfonic acid according to item 2, obtainable (obtained) by subjecting a vinyl sulfonate to a metal removal treatment by bringing the vinyl sulfonate into contact with a strongly-acidic ion-exchange resin, and purifying the product obtained from the metal removal treatment using the thin-film distillation apparatus according to item 6.

Item 8. An electric/electronic material comprising the vinyl sulfonic acid according to item 1 or 2.

Item 9. An electric/electronic material comprising the vinyl sulfonic acid homopolymer or copolymer according to item 3.

Item 10. A polymer electrolyte membrane for a fuel cell comprising the vinyl sulfonic acid homopolymer or copolymer according to item 3.

Item E. A fuel cell comprising the polymer electrolyte membrane according to item 10.

Item 11. A photoresist composition comprising the vinyl sulfonic acid according to item 1 or 2 or the vinyl sulfonic acid homopolymer or copolymer according to item 3.

Item 12. A conductive polymer composition comprising the vinyl sulfonic acid homopolymer or copolymer according to item 3 as a dopant.

The present invention will now be described in more detail.

In the present specification, unless stated otherwise, "ppm" refers to "weight ppm" and "ppb" refers to "weight ppb".

1. Vinyl Sulfonic Acid (1) Double Bond Content

The vinyl sulfonic acid according to the present invention has a double bond content of 95 wt. % or more, especially 97 wt. % or more, and more especially 99 wt. % or more.

In the present invention, "double bond content" means a value determined by quantifying an amount of double bonds and calculating this in terms of a purity of the vinyl sulfonic acid, or in other words, multiplying a number of moles of double bonds in 100 g of the vinyl sulfonic acid by 1 gram equivalent of the vinyl sulfonic acid.

A double bond content can be determined from the following formula based on a measured iodine value.

$$\text{Double bond content(wt. \%)} = (\text{iodine value}) \times (108.1/2)/126.9$$

(Here, 108.1 is the molecular weight of vinyl sulfonic acid, and 126.9 is the atomic weight of iodine.)

(2) Metal Content

The vinyl sulfonic acid according to the present invention has a (i) sodium (Na) content of 1 ppm or less, preferably 500 ppb or less, and especially preferably 300 ppb or less. Further, the vinyl sulfonic acid according to the present invention has (ii) a content of at least one metal selected from the group consisting of alkali earth metal and first row transition metal of 1 ppm or less, preferably 800 ppb or less, and especially preferably 500 ppb or less.

Especially, the vinyl sulfonic acid according to the present invention has a (i) sodium (Na) content of 100 ppb or less, preferably 50 ppb or less, and especially preferably 10 ppb or less. Further, the vinyl sulfonic acid according to the present invention has (ii) a content of at least one metal selected from the group consisting of alkali earth metal and first row transition metal of 100 ppb or less, preferably 50 ppb or less, and especially preferably 20 ppb or less.

Examples of alkali earth metal include calcium (Ca).

Examples of first row transition metal include iron (Fe), chromium (Cr), and nickel (Ni).

An example of a preferred vinyl sulfonic acid according to the present invention has:
(i) a sodium (Na) content of 1 ppm or less,
(ii) a calcium (Ca) content of 1 ppm or less, and
(iii) a content of at least one metal selected from first row transition metal of 1 ppm or less.

An example of a more preferred vinyl sulfonic acid has:
(i) a sodium (Na) content of 1 ppm or less,
(ii) a calcium (Ca) content of 1 ppm or less, and
(iii) a content of the metals iron (Fe), chromium (Cr), and nickel (Ni) of 1 ppm or less, respectively.

An example of an especially preferred vinyl sulfonic acid has:
(i) a sodium (Na) content of 100 ppb or less,
(ii) a calcium (Ca) content of 100 ppb or less, and
(iii) a content of at least one metal selected from first row transition metal of 100 ppb or less.

An example of an even more especially preferred vinyl sulfonic acid has:
(i) a sodium (Na) content of 100 ppb or less,
(ii) a calcium (Ca) content of 100 ppb or less, and
(iii) a content of the metals iron (Fe), chromium (Cr), and nickel (Ni) of 100 ppb or less, respectively.

Further, it is also preferred that the vinyl sulfonic acid has a low lithium (Li), magnesium (Mg), aluminum (Al), potassium (K), manganese (Mn), copper (Cu), zinc (Zn), zirconium (Zr), tin (Sn), and lead (Pb) content, respectively. A vinyl sulfonic acid having a respective content of these metals of about 100 ppb or less, and preferably about 50 ppb or less, can be preferably used.

The metal content can be measured based on a well-known method. For example, methods such as ICP mass spectrometry (ICP-MS), ICP emission spectrometric analysis (ICP-OES/ICP-AES), and atomic adsorption spectrometry can be used. Generally, it is preferred to use ICP-MS.

The vinyl sulfonic acid according to the present invention has reduced impurity and metal contents, and can be preferably used as a material for an electric/electronic material. In other words, the vinyl sulfonic acid according to the present invention can be preferably used as a material in a production of an electric/electronic material.

Examples of an electric material include a fuel cell electrolyte membrane, an organic EL thin film, and a battery peripheral material. Examples of an electronic material include a semiconductor peripheral material, a conductive polymer material, and a circuit board material.

For example, a homopolymer formed by impregnating the vinyl sulfonic acid in a substrate and then carrying out homopolymerization, or a copolymer formed by impregnating the vinyl sulfonic acid in a substrate and then copolymerizing with another polymerizable monomer, can be used as a fuel cell polymer electrolyte.

Further, the vinyl sulfonic acid, or a homopolymer formed by polymerizing just this vinyl sulfonic acid or a copolymer formed by copolymerizing the vinyl sulfonic acid with another polymerizable monomer, can be used as a material for a photoresist composition, a polymer binder or a separator for a battery. In addition, the product obtained by polymerization of the vinyl sulfonic acid can be used as an anionic polymer acid dispersant in a polishing slurry for semiconductor fabrication, or as a conductive polymer dopant used in an EL device, such as an organic light-emitting diode (OLED).

2. Vinyl Sulfonic Acid Production Method

A method for producing the vinyl sulfonic acid according to the present invention is not especially limited, as long as the vinyl sulfonic acid has the above-described characteristics. Vinyl sulfonic acids obtained by the following production methods are preferred.

Production method 1: A method for producing the vinyl sulfonic acid, comprising a step of subjecting a vinyl sulfonate to a metal removal treatment, wherein the metal removal rate in the metal removal treatment represented by the following formula is 95% or more:

$$\text{Metal removal rate(\%)} = \{(\text{acid value after metal removal treatment})/(\text{acid value before metal removal treatment})\} \times 100.$$

Production method 2: A method for producing the vinyl sulfonic acid, comprising a step of subjecting a vinyl sulfonate to a metal removal treatment, wherein the metal removal treatment is carried out using a strongly-acidic ion-exchange resin.

Production method 3: The production method according to the above-described production method 1 or 2, further comprising a step of purifying the product obtained from the metal removal treatment using a thin-film distillation apparatus.

Production method 4: The production method according to the above-described production method 3, wherein the thin-film distillation apparatus is an apparatus in which all or a part of a contact with the vinyl sulfonic acid or a composition thereof are formed from a material having a high corrosion resistance.

Production method 5: The production method according to the above-described production method 3, wherein the thin-film distillation apparatus is an apparatus in which all or a part of a contact with the vinyl sulfonic acid or a composition thereof are made from tantalum.

Production method 6: The production method according to the above-described production method 4 or 5, wherein the thin-film distillation apparatus comprises:

a distillation tower for evaporating a distillation raw material;

a vinyl sulfonic acid vapor outlet which is provided in a middle section of the distillation tower; and a cooling device which is arranged externally to the distillation tower for condensing the vinyl sulfonic acid vapor obtained from the outlet.

Examples of the raw material vinyl sulfonate include sodium salts, potassium salts, lithium salts, or a mixture thereof. Of these, it is especially preferred to use sodium vinyl sulfonate.

The vinyl sulfonate may be provided in the form of a composition. For example, in addition to a vinyl sulfonate, a composition including an isethionate or a salt of a bis-sulfoethyl ether may also be used as the raw material. When using a composition, a ratio of the vinyl sulfonate based on the whole composition is generally about 25 wt. % or more.

The term "metal removal treatment" refers to a treatment in which metal is removed from the vinyl sulfonate and substituted with hydrogen. In other words, the term "metal removal treatment" refers to a treatment in which metal ions are removed from the vinyl sulfonate, which is converted into a vinyl sulfonic acid.

The metal removal treatment step can be illustrated by the following general formula.

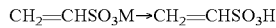

$$CH_2=CHSO_3M \rightarrow CH_2=CHSO_3H$$

(wherein M represents a metal to form a salt, specifically, sodium, potassium and the like)

The metal removal rate is preferably 95% or more, especially preferably 97% or more, and more especially preferably 99% or more.

The metal removal rate refers to a value calculated by the following formula.

Metal removal rate(%)={(acid value after metal removal treatment)/(acid value before metal removal treatment)}×100.

Stated another way, the metal removal rate is the rate of the metal contained in the raw material converted into hydrogen. For example, if a sodium salt is used as the raw material, the metal removal rate is the conversion rate from sodium into hydrogen (the sodium conversion rate). Stated even another way, the metal removal rate is the rate of the decrease of the metal salt compound contained in the raw material.

The metal removal rate may be determined by measuring an acid value based on a known method. For example, the metal removal rate may be determined by measuring an acid value based on neutralization titration.

If the metal removal rate is 95% or more, the degradation of the compound or impact thereof is substantially reduced. Further, this also allows the introduction of thin-film distillation into the purification step carried out after the metal removal treatment, thereby enabling large-scale distillation to be carried out at a high recovery rate. In addition, a high-quality vinyl sulfonic acid can be obtained, which allows a vinyl sulfonic acid having little discoloration when it is distilled off in the distillation step to be obtained. Moreover, a vinyl sulfonic acid which hardly changes in color over time can be obtained.

The metal removal treatment method is not especially limited, although it is preferred to use a strongly-acidic ion-exchange resin. In other words, it is preferred to carry out the metal removal treatment by bringing the vinyl sulfonate into contact with the strongly-acidic ion-exchange resin.

The method for bringing the vinyl sulfonate into contact with the strongly-acidic ion-exchange resin can be carried out by a common method. However, it is preferred to fill the ion-exchange resin into a column and pass an aqueous solution of the vinyl sulfonate therethrough, as this allows ion exchange to be performed reliably.

The type of the strongly-acidic ion-exchange resin is not especially limited, as long as the advantageous effects of the present invention can be enjoyed. A known ion-exchange resin may be appropriately selected. For example, a compound having a strong acid group on a side chain of a crosslinked insoluble organic polymer compound can be used. Examples of the strong acid group include a sulfuric acid group, a phosphoric acid group, and a sulfonic acid group.

Specific examples of the strongly-acidic ion-exchange resin include Diaion (registered trademark) (SK1B, SK116, PK216 etc.), Amberlite (registered trademark) (IR-120B, IR-124 etc.), Dowex (registered trademark) (50wx8, HCR-S, Monosphere 650C etc.), and Lewatit (registered trademark) (S-100 etc.).

By carrying out the metal removal treatment using the strongly-acidic ion-exchange resin, the vinyl sulfonate content can be reduced by a high ratio, degradation of the compound can be suppressed, and the yield can be improved.

Further, a vinyl sulfonic acid having excellent quality and hardly any discoloration can be obtained.

Further, by using the strongly-acidic ion-exchange resin, the metal removal treatment can be carried out efficiently with just one treatment.

In addition, this also allows the introduction of thin-film distillation into the subsequent purification step, thereby enabling large-scale distillation to be carried out.

From perspectives such as reducing a generation of gases and further improving a recovery rate in the distillation, the metal removal rate in the metal removal treatment using the strongly-acidic ion-exchange resin is preferably 95% or more, especially preferably 97% or more, and more especially preferably 99% or more.

It is preferred to further purify the treated product obtained from the metal removal treatment by a known method. The term "product obtained from the metal removal treatment" means the product obtained by performing the metal removal treatment on the vinyl sulfonate or composition thereof. Specifically, this term means the vinyl sulfonic acid or composition thereof obtained from the metal removal treatment.

The purification method can be appropriately set from among known methods. However, purification carried out by distillation, especially thin-film distillation, is preferred.

By carrying out the purification by thin-film distillation, a vinyl sulfonic acid can be obtained which has excellent quality, little discoloration when it is distilled off, and hardly any problems with discoloration over time. Further, this also enables large-scale purification to be carried out at a high recovery rate.

Especially, it is preferred to carry out purification by thin-film distillation of the treated product obtained from the metal removal treatment carried out so that the metal removal rate of the vinyl sulfonate is 95% or more.

Further, it is preferred to carry out purification by thin-film distillation of the treated product obtained from the metal removal treatment carried out by bringing the vinyl sulfonate into contact with the strongly-acidic ion-exchange resin.

Especially, it is preferred to subject the treated product obtained from the metal removal treatment, which was carried out by bringing the vinyl sulfonate into contact with the strongly-acidic ion-exchange resin so that the metal removal rate is 95% or more, to thin-film distillation.

Consequently, degradation of the compound during distillation is reduced, and a recovery rate can be further improved. Further, a generation of gases during distillation can be reduced, and a degree of vacuum can be stably maintained. In addition, continuous distillation becomes possible, and large-scale distillation can be carried out. Moreover, the residue can be obtained as a fluid product rather than a high-viscosity solid. Therefore, cleaning of the apparatus and equipment is easier. Still further, the obtained vinyl sulfonic acid has a high quality, and a basically colorless vinyl sulfonic acid can be obtained when it is distilled off. Moreover, a vinyl sulfonic acid which hardly changes in color over time can be obtained.

The thin-film distillation can be carried out by a known method.

The thin-film distillation conditions can be appropriately set. However, usually, the temperature is about 150 to 250° C., and preferably about 150 to 230° C.

In addition, the pressure is usually about 10 to 400 Pa, and preferably about 10 to 200 Pa.

Under such conditions, degradation and polymerization can be further suppressed.

The thin-film distillation can optionally be carried out twice or more, and can even be carried out continuously.

A known thin-film distillation apparatus can be used. However, an apparatus in which all or a part of a contact with the vinyl sulfonic acid or a composition thereof is formed from a material having a high corrosion resistance is preferred.

In addition, so that the distillation residue does not contaminate the product, the thin-film distillation apparatus preferably has a vinyl sulfonic acid vapor outlet which is provided in a middle section of the distillation tower, and a cooling device which is arranged externally to the distillation tower.

Specific examples of the thin-film distillation apparatus include the apparatus described in the following section 3.

The method for producing the vinyl sulfonic acid according to the present invention may optionally include further steps to those described above, such as a step of purifying the raw material.

Further, known technology relating to the production of vinyl sulfonic acids may also be included as necessary.

From the above-described production methods, a vinyl sulfonic acid can be obtained which has a high double bond content and a low metal content. In other words, the vinyl sulfonic acid used in the present invention includes the vinyl sulfonic acids which can be obtained by any of production methods 1 to 6. A vinyl sulfonic acid obtained by the above-described production methods has little discoloration and hardly any change in color over time.

3. Apparatus

The present invention provides a thin-film distillation apparatus which can be preferably used in the method for producing the vinyl sulfonic acid. In other words, the present invention provides a thin-film distillation apparatus for vinyl sulfonic acid production, or a thin-film distillation apparatus for vinyl sulfonic acid purification.

In the thin-film distillation apparatus according to the present invention, all or a part of a contact with the vinyl sulfonic acid or a composition thereof is formed from a material having a high corrosion resistance.

The term "a contact with the vinyl sulfonic acid or a composition thereof" (hereinafter also referred to as "vinyl sulfonic acid contact region") means, for example, a region that is in contact with the vinyl sulfonic acid composition serving as the distillation raw material after it has undergone the metal removal treatment, the evaporated vinyl sulfonic acid vapor, or the condensed vinyl sulfonic acid formed from the vinyl sulfonic acid vapor. These regions are also referred to as "liquid contact region" and/or "gas contact region".

Examples of the members included in the vinyl sulfonic acid contact region include a liquid feed pipe, the inner walls of the distillation tower, a stirring member, a wiper member, a cooling member, a stirring seal member, a distillation raw material introduction port, a distillate line, a receiver, a residue discharge line and the like.

Examples of the material having a high corrosion resistance include JIS standard R-3503 borosilicate glass-1 and metal materials determined as being completely resistant to corrosion by a corrosion resistance test.

JIS Standard R-3503 borosilicate glass-1 is a glass which, based on the JIS (Japanese Industrial Standards) standard R-3503, has been given a rating of having a linear thermal expansion coefficient of $3.5 \times 10^{-6} \cdot K^{-1}$ or less and an alkali elution amount of 0.10 mL/g or less or 31 µg/g or less.

Further, the term "metal materials determined as being completely resistant to corrosion by a corrosion resistance test" refers to metal materials having a rate of corrosion of 0.05 mm/year or less. Examples of the corrosion resistance test include a method in which, based on the method of item a. in "Chemical Apparatus Handbook" (edited by the Society for Chemical Engineers, Japan, published by Maruzen, 1970, p. 500), a test piece is dipped in 165° C. vinyl sulfonic acid and then the change in weight and the change in appearance after a certain time period are measured.

Examples of the glass which is categorized as JIS Standard borosilicate glass-1 include products such as Pyrex (registered trademark), Hario (registered trademark), and Duran (registered trademark).

Further, examples of the metal material determined as being completely resistant to corrosion include tantalum.

If the vinyl sulfonic acid contact region is formed from the material having a high corrosion resistance, contamination of impurities from the material or the region can be suppressed. Conventionally, a material such as SUS was used as a metal for the vinyl sulfonic acid contact region, so that impurities from this material contaminated the vinyl sulfonic acid. However, according to the above-described configuration, the level of contamination of impurities due to the material is reduced.

An example in which tantalum is used as the material having a high corrosion resistance will now be described.

The term "all or a part of the vinyl sulfonic acid contact region is made from tantalum", or in other words, formed from tantalum, includes a case in which all or at least one of the members comprised the vinyl sulfonic acid contact region is/are made from tantalum. Further, this also includes a case in which at least a part of one member constituting the vinyl sulfonic acid contact region is made from tantalum, specifically, is formed from tantalum.

Further, the term "made from tantalum" means being formed from a material which essentially does not include components other than tantalum. In other words, the term "made from tantalum" means being formed from a material having a content of components other than tantalum of only less than 0.3 wt. %, and especially less than 300 ppm.

Examples of the apparatus according to the present invention include an apparatus in which only the stirring rotation member and/or wiper member is made from tantalum, an apparatus in which the whole stirring rotation member is made from tantalum, an apparatus in which a part of the wiper member is made from tantalum, and an apparatus in which all or a part of the thin-film forming member is made from tantalum. It is especially preferred that the members or sections which conventionally are formed from a metal are made from tantalum.

More specifically, for a falling thin-film distillation apparatus, an example thereof includes an apparatus in which all or a part of the stirring rotation member and wiper member is made from tantalum.

Further, for a centrifugal thin-film distillation apparatus, an example thereof includes an apparatus in which the rotor member and the disk member are made from tantalum.

An example of the apparatus is the following apparatus A, which comprises:
   an introduction port for the distillation raw material,
   a distillation tower for evaporating the introduced raw material,
   a stirring drive member arranged at the apex of the distillation tower,
   a stirring rotation member made from tantalum, which is arranged inside the distillation tower,
   a wiper member comprising at least a section made from tantalum, which is connected to the stirring rotation member,
   a vacuum pump suction port connected to the distillation tower,
   a cooling member arranged inside the distillation tower,
   a vinyl sulfonic acid receiver which receives the vinyl sulfonic acid condensed by the cooling device, and
   a residue receiver arranged on the bottom of the distillation tower.

For example, the apparatus illustrated in FIG. 1 is included in this example.

Further, an example of another apparatus includes an apparatus configured so that the vinyl sulfonic acid vapor exits from a middle section of the distillation tower, and is delivered to a cooling member provided externally to the distillation tower.

Such an apparatus further suppresses contamination of the distillation residue in the vinyl sulfonic acid vapor because the cooling member is provided externally to the distillation tower. Further, since the vinyl sulfonic acid vapor is discharged from a middle section of the distillation tower, contamination of impurities due to corrosion and the like of the tower apex section of the stirring drive member and the like can be suppressed.

The term "middle section" means, based on a length from the apex to the bottom of the distillation tower being 100, a position which is about 30 to 60, and preferably 40 to 50, the way down from the apex.

An example of such an apparatus is the following apparatus B, which comprises:
   an introduction port for the distillation raw material,
   a distillation tower for evaporating the introduced raw material,
   a stirring drive member arranged at the apex of the distillation tower,
   a stirring rotation member made from tantalum, which is arranged inside the distillation tower,
   a wiper member comprising at least a section made from tantalum, which is connected to the stirring rotation member,
   a residue receiver arranged on the bottom of the distillation tower,
   a vinyl sulfonic acid outlet which is provided in a middle section of the distillation tower,
   a cooling device which is arranged externally to the distillation tower for condensing the vinyl sulfonic acid vapor from the outlet,
   a vinyl sulfonic acid receiver which receives the vinyl sulfonic acid condensed by the cooling device, and
   a vacuum pump suction port connected to the vinyl sulfonic acid receiver.

For example, the apparatus illustrated in FIG. 2 is included in this example.

The distillation tower usually has a heating means. Further, the distillation tower may optionally have a known means for sensing the temperature and the like.

The stirring drive member is a power member for rotating the stirring rotation member. The stirring drive member is usually sealed by a stirring seal member to prevent corrosion due to vapor produced in the distillation tower.

By carrying out purification using the above-described apparatuses, a vinyl sulfonic acid can be obtained which has a high double bond content and a low metal content. In other words, the vinyl sulfonic acid used in the present invention includes a vinyl sulfonic acid obtained by carrying out purification using the above-described thin-film distillation apparatuses.

Especially, a vinyl sulfonic acid having:
   a double bond content of 95 wt. % or more; and
   (i) a sodium (Na) content of 100 ppb or less; and
   (ii) a content of at least one metal selected from the group consisting of alkali earth metal and first row transition metal of 100 ppb or less, can be suitably produced by carrying out purification using the above-described apparatuses A and B.

Especially, the inventive vinyl sulfonic acid can be preferably produced using the apparatus B.

4. Homopolymer

The vinyl sulfonic acid homopolymer according to the present invention can be obtained by polymerizing the above-described vinyl sulfonic acid as a homopolymer. In other words, the present invention provides a homopolymer having the above-described vinyl sulfonic acid as a constituent component.

Since the vinyl sulfonic acid homopolymer according to the present invention is obtained from a vinyl sulfonic acid having a high double bond content and a low metal content, the homopolymer has hardly any impurities, a low metal content, and excellent quality.

Preferably, as the metal content, the polymer according to the present invention has (i) a sodium (Na) content of 1 ppm or less, and (ii) a content of at least one metal selected from the group consisting of alkali earth metal and first row transition metal of 1 ppm or less.

Especially:
(i) a sodium (Na) content of 1 ppm or less,
(ii) a calcium (Ca) content of 1 ppm or less, and
(iii) a content of at least one metal selected from first row transition metal of 1 ppm or less.

More preferably:
(i) a sodium (Na) content of 1 ppm or less,
(ii) a calcium (Ca) content of 1 ppm or less, and
(iii) a content of the metals iron (Fe), chromium (Cr), and nickel (Ni) of 1 ppm or less, respectively.

Especially preferably, the polymer according to the present invention has, as the metal content, (i) a sodium (Na) content of 100 ppb or less, and (ii) a content of at least one metal selected from the group consisting of alkali earth metal and first row transition metal of 100 ppb or less.

Especially, (i) a sodium (Na) content of 100 ppb or less, (ii) a calcium (Ca) content of 100 ppb or less, and (iii) a content of at least one metal selected from first row transition metal of 100 ppb or less.

More preferably, (i) a sodium (Na) content of 100 ppb or less, (ii) a calcium (Ca) content of 100 ppb or less, and (iii) a content of the metals iron (Fe), chromium (Cr), and nickel (Ni) of 100 ppb or less, respectively.

The molecular weight of the homopolymer can be based on the purpose, and may be, but is not limited to, about 500 to 400,000, and especially about 2,000 to 300,000, in terms of weight average molecular weight as measured by size exclusion chromatography (hereinafter, "SEC").

Although SEC can be divided into gel permeation chromatography (GPC), in which the mobile phase is an organic solvent, and gel filtration chromatography (GFC), in which the mobile phase is an aqueous solution, the SEC in the present specification includes both of these methods.

The vinyl sulfonic acid homopolymer according to the present invention has a low impurity content, a low metal content, excellent quality, and can be preferably used as a raw material for an electric/electronic material. In other words, the vinyl sulfonic acid homopolymer according to the present invention can be preferably used as a raw material in the production of an electric/electronic material.

Examples of the electric material include an electrolyte membrane for a fuel cell, an organic EL thin film, and a battery peripheral material.

Examples of the electronic material include a semiconductor peripheral material, a conductive polymer material, and a circuit board material.

More specifically, the polymer according to the present invention can be used as a polymer for a fuel cell electrolyte membrane, a polymer for a photoresist, a conductive polymer dopant, a polymer for an organic EL thin film and the like.

Especially, the polymer according to the present invention can be preferably used for the electronic material, for example in fields in which it is important to prevent metal contamination, such as semiconductors.

5. Homopolymer Production Method

A method for producing the vinyl sulfonic acid homopolymer is not especially limited. However, generally, the method is carried out by radical polymerization, photopolymerization, or radiation polymerization.

The radical polymerization is carried out by adding a small amount of an initiator to the vinyl sulfonic acid or an aqueous solution thereof. As the initiator, a peroxide, a persulfate, an azo compound or a redox initiator can be used.

The photopolymerization is carried out by irradiating light on the vinyl sulfonic acid or an aqueous solution thereof. For example, the irradiation can be carried out using solar rays, UV rays and the like. During the irradiation, a photopolymerization initiator, a photopolymerization promoter and the like may optionally be added. It is especially preferred to carry out the photopolymerization in the presence of N,N-dimethylformamide.

The radiation polymerization is carried out by irradiating radioactive rays on the vinyl sulfonic acid or an aqueous solution thereof.

To further reduce the metal content, the homopolymer according to the present invention may be purified by a known method. The purification method is not especially limited. Examples thereof include solvent reprecipitation and an ion-exchange method.

The solvent reprecipitation is a purification method in which a polymer is dissolved in as small an amount of solvent as possible, and then the resultant mixture is added dropwise to a solvent having a lower solubility for this polymer to cause a precipitate to form. The ion-exchange method is a purification method in which a polymer is dissolved in a solvent, and the metal ions are exchanged using an ion-exchange resin.

6. Copolymer

The copolymer according to the present invention is a copolymer which has the above-described vinyl sulfonic acid as a constituent component. More specifically, the copolymer according to the present invention comprises the above-described vinyl sulfonic acid as an essential monomer.

The vinyl sulfonic acid copolymer according to the present invention can be obtained by copolymerizing the above-described vinyl sulfonic acid with one or two or more other monomers.

These "other monomers" are polymerizable compounds different from the above-described vinyl sulfonic acid, which serve as one of the constituent components of the copolymer.

These other monomers are not especially limited, as long as they are a substance that is copolymerizable with the above-described vinyl sulfonic acid. A vinyl monomer can be preferably used as the other monomer.

Examples of the vinyl monomer include a vinyl monomer containing a sulfonic acid group, a vinyl monomer containing a carboxyl group, a vinyl monomer containing an ester group, a vinyl monomer containing nitrogen, a vinyl monomer containing halogen, an aliphatic vinyl monomer, and an aromatic vinyl monomer.

Specifically, examples of the vinyl monomer containing the sulfonic acid group include acrylamido methylpropane sulfonic acid, styrene sulfonic acid, and (meth)allyl sulfonic acid.

Examples of the vinyl monomer containing the carboxyl group include (meth)acrylic acid.

Examples of the vinyl monomer containing the ester group include a (meth)acrylic acid ester and vinyl acetate.

Examples of the (meth)acrylic acid ester include (meth)acrylic acid esters of monoalcohols, such as methyl (meth)acrylate, ethyl(meth)acrylate, and hydroxyethyl(meth)acrylate, and (meth)acrylic acid esters of polyhydric alcohols, such as trimethylolpropane tri(meth)acrylate and tetraethylene glycol di(meth)acrylate.

Examples of the vinyl monomer containing nitrogen include allylamine, vinylpyrrolidone, vinylimidazole, vinylpyridine, vinylformamide, (meth)acrylamide, propylacrylamide, (meth)acrylonitrile, and cyanomethylstyrene.

Examples of the vinyl monomer containing halogen include vinyl chloride, chloroprene, (meth)allylchloride, and chloroethyl vinyl ether.

Examples of the aliphatic vinyl monomer include ethylene and propylene.

Examples of the aromatic vinyl monomer include styrene, α-methyl styrene, chloromethyl styrene, and divinyl benzene.

As the above-described other monomers, just one kind or two kinds or more may be used.

For example, the copolymer according to the present invention includes a copolymer obtained by copolymerizing the vinyl sulfonic acid with at least one kind selected from the group consisting of (meth)acrylic acid, a (meth)acrylic acid ester, a (meth)acrylic acid amide, and a (meth)acrylonitrile.

Further, in the present specification, "(meth)acrylic acid" means acrylic acid and/or methacrylic acid. Similarly, "(meth)acrylic acid ester" means acrylic acid ester and/or methacrylic acid ester, "(meth)acrylic acid amide" means acrylic acid amide and/or methacrylic acid amide, and "(meth)acrylonitrile" means acrylonitrile and/or methacrylonitrile.

It is preferred that the above-described monomer has a low metal content.

For example, it is preferred to use a monomer having:
(i) a sodium (Na) content of 100 ppb or less, especially 50 ppb or less, and
(ii) a content of at least one metal selected from the group consisting of alkali earth metal and first row transition metal of 100 ppb or less, and especially about 50 ppb or less.

Examples of the alkali earth metal include calcium (Ca).

Examples of the first row transition metal include iron (Fe), chromium (Cr), and nickel (Ni).

It is especially preferred to use a monomer having (i) a sodium (Na) content of 100 ppb or less, and especially 50 ppb or less, (ii) a calcium (Ca) content of 100 ppb or less, and especially 50 ppb or less, and (iii) a content of the metals iron (Fe), chromium (Cr), and nickel (Ni), respectively, of 100 ppb or less, and especially 50 ppb or less.

The reduction of the metal content in these monomers can be carried out by a known method, and is usually carried out by distillation or sublimation.

During this process, to prevent polymerization of the monomer, it is preferred to carry out the process under a reduced pressure to avoid a high temperature, and also to add a suitable polymerization inhibitor.

Examples of the polymerization inhibitor include hydroquinone, hydroquinone monomethyl ether, phenothiazine, 4-tertbutylcatechol, 3,5-dibutyl-4-hydroxytoluene, and 2,6-dinitro-p-cresol.

Since the vinyl sulfonic acid copolymer according to the present invention is obtained from a vinyl sulfonic acid having a high double bond content and a low metal content, the copolymer has a low impurity content, a low metal content, and excellent quality.

The copolymer according to the present invention comprises copolymers having in the copolymer (i) a sodium (Na) content of 1 ppm or less, and (ii) a content of at least one metal selected from the group consisting of alkali earth metal and first row transition metal of 1 ppm or less.

Especially, the copolymer according to the present invention comprises copolymers having:
(i) a sodium (Na) content of 1 ppm or less,
(ii) a calcium (Ca) content of 1 ppm or less, and
(iii) a content of at least one metal selected from first row transition metal of 1 ppm or less.

More especially, the copolymer according to the present invention comprises copolymers having:
(i) a sodium (Na) content of 1 ppm or less,
(ii) a calcium (Ca) content of 1 ppm or less, and
(iii) a content of the metals iron (Fe), chromium (Cr), and nickel (Ni) of 1 ppm or less, respectively.

The copolymer according to the present invention comprises copolymers having in the copolymer (i) a sodium (Na) content of 200 ppb or less, and (ii) a content of at least one metal selected from the group consisting of alkali earth metal and first row transition metal of 200 ppb or less.

Especially, the copolymer according to the present invention comprises copolymers having:
(i) a sodium (Na) content of 200 ppb or less,
(ii) a calcium (Ca) content of 200 ppb or less, and
(iii) a content of at least one metal selected from first row transition metal of 200 ppb or less.

More especially, the copolymer according to the present invention comprises copolymers having:
(i) a sodium (Na) content of 200 ppb or less,
(ii) a calcium (Ca) content of 200 ppb or less, and
(iii) a content of the metals iron (Fe), chromium (Cr), and nickel (Ni) of 200 ppb or less, respectively.

A ratio of the monomers constituting the copolymer can be set based on the purpose, and is not especially limited. However, usually, this ratio is 1 to 99 mole %, and especially about 10 to 90 mole %, of the vinyl sulfonic acid to 99 to 1 mole %, and especially about 90 to 10 mole %, of the other monomer.

For example, the copolymer according to the present invention comprises copolymers obtained by polymerizing 10 to 90 mole % of the vinyl sulfonic acid and 90 to 10 mole % of the other monomer.

The molecular weight of the copolymer can be set based on the purpose, and may be, but is not limited to, about 500 to 50,000,000, and especially about 2,000 to 5,000,000, in terms of weight average molecular weight as measured by SEC.

The vinyl sulfonic acid copolymer according to the present invention has a low metal content, and can be preferably used as a raw material for an electric/electronic material.

Examples of the electric material include a fuel cell electrolyte membrane, an organic EL thin film, and a battery peripheral material.

Examples of the electronic material include a semiconductor peripheral material, a conductive polymer material, and a circuit board material.

More specifically, the copolymer according to the present invention can be used as a material and/or raw material thereof for a polymer for a fuel cell electrolyte membrane, a polymer for a photoresist, a conductive polymer dopant, a polymer for an organic EL thin film and the like.

Especially, the copolymer according to the present invention can be preferably used for the electronic material, for example in fields in which it is important to prevent metal contamination, such as semiconductors.

7. Copolymer Production Method

A method for producing the vinyl sulfonic acid copolymer is not especially limited. However, generally, the method is carried out by radical polymerization, photopolymerization, or radiation polymerization.

The radical polymerization is carried out by mixing the vinyl sulfonic acid or aqueous solution thereof and the other monomer or aqueous solution thereof, adding a small amount of an initiator to the resultant mixture, and heating. As the initiator, a peroxide, a persulfate, an azo compound or a redox initiator can be used.

The photopolymerization is carried out by mixing the vinyl sulfonic acid or aqueous solution thereof and the other monomer or aqueous solution thereof, and irradiating light on the resultant mixture. For example, the irradiation can be carried out using solar rays, UV rays and the like. Further, a photopolymerizable crosslinking agent, a photopolymerization initiator, a photopolymerization promoter and the like may optionally be added. It is especially preferred to carry out the photopolymerization in the presence of N,N-dimethylformamide.

The radiation polymerization is carried out by mixing the vinyl sulfonic acid or aqueous solution thereof and the other monomer or aqueous solution thereof, and irradiating radioactive rays on the resultant mixture.

When using two or more kinds of the other monomer, these may be simultaneously mixed, or may be successively mixed.

To further reduce the metal content, the copolymer according to the present invention may be purified by a known method. The purification method is not especially limited. Examples thereof include a solvent reprecipitation and an ion-exchange method.

The solvent reprecipitation is a purification method in which a polymer is dissolved in as small an amount of solvent as possible, and then the resultant mixture is added dropwise to a solvent having a lower solubility for this polymer to cause a precipitate to form. The ion-exchange method is a purification method in which a polymer is dissolved in a solvent, and the metal ions are exchanged using an ion-exchange resin.

8. Electric/Electronic Material

The present invention provides an electric/electronic material which comprises the above-described vinyl sulfonic acid, or the homopolymer or copolymer thereof. In other words, the vinyl sulfonic acid, or the homopolymer or copolymer thereof, according to the present invention can be preferably used as a raw material for producing the electric/electronic material.

In the present invention, the term "electric/electronic material" means an electric and/or electronic material.

Examples of the electric/electronic material comprising the vinyl sulfonic acid according to the present invention include a polymer electrolyte membrane for a fuel cell, an organic EL thin film, a battery peripheral material, a semiconductor peripheral material, a conductive polymer material, and a circuit board material.

Further, examples of electric/electronic materials comprising the homopolymer and/or copolymer of the vinyl sulfonic acid according to the present invention include a polymer electrolyte membrane for a fuel cell, an organic EL thin film, a battery peripheral material, a semiconductor peripheral material, a conductive polymer material, and a circuit board material.

It is especially preferred to use the homopolymer and/or copolymer of the vinyl sulfonic acid according to the present invention as a material for a polymer electrolyte membrane for a fuel cell, a photoresist composition, and a conductive polymer composition.

(1) Polymer Electrolyte Membrane for a Fuel Cell

The polymer electrolyte membrane can be obtained by forming a film of the homopolymer and/or copolymer of the vinyl sulfonic acid according to the present invention.

The film-forming method is not especially limited. Examples of methods which can be used include forming the film from a solution state (solution casting) or forming the film from a melt state (melt pressing or melt extrusion). The film thickness is not especially limited, and can be appropriately set in order to obtain the desired characteristics. For solution casting, the film thickness can be controlled based on the solution concentration or based on the thickness of the coating on the substrate. For melt pressing or melt extrusion, the film thickness can be controlled based on the spacer thickness, the die gap, or the pick-up speed. In addition, during production of the polymer electrolyte membrane, additives which are usually used in polymers, such as a plasticizer, a stabilizing agent, and a release agent, may be used to the extent that does not hinder the object of the present invention.

The obtained polymer electrolyte membrane can be preferably used for a fuel cell. The fuel cell production method is not especially limited. The fuel cell production can be carried out based on a known method, as long as such method uses a membrane using the polymer according to the present invention as the polymer electrolyte membrane. Further, the structure of the fuel cell is not especially limited, and a known structure can be used. Examples thereof include a structure formed from an oxygen electrode, a fuel electrode, an electrolyte membrane between the oxygen electrode and the fuel electrode, an oxidant distribution plate having an oxidant channel arranged on an external side of the oxygen electrode, and a fuel distribution plate having a fuel channel arranged on an external side of the fuel electrode.

(2) Photoresist Composition

The photoresist composition can be produced by, based on a common method, mixing the vinyl sulfonic acid, or the homopolymer and/or copolymer thereof, according to the present invention in water or an organic solvent. The photoresist composition may optionally comprise other components, such as another water-soluble polymer or alkali-soluble polymer, a surfactant, a photopolymerizable crosslinking agent, a photopolymerization initiator, a sensitizer, and a photo-acid-generating agent.

A ratio of the polymer can be appropriately set based on whether water or an organic solvent is used, the other component, and the lithography conditions.

A photosensitive film pattern for a semiconductor device can be formed using the above-described photoresist composition to form a resist film.

Although the resist film can also be formed by a common method, generally, the resist film is formed by coating the photoresist composition on a substrate, then solidifying the composition by heating, and volatilizing the solvent.

Examples of the coating method include rotation coating, cast coating, roll coating and the like. Further, examples of the substrate include a silicon wafer, glass, alumina, Teflon (registered trademark) and the like.

The pattern can be formed by exposing the formed resist film to light, removing excess portions, performing etching based on the pattern, and finally completely removing the resist. Examples of the exposure source include a semiconductor laser, a metal halide lamp, a high-pressure mercury lamp, an excimer laser, and an electron beam.

(3) Conductive Polymer Composition

The vinyl sulfonic acid homopolymer or copolymer according to the present invention can be used as a conductive polymer dopant.

Examples of the conductive polymer include polythiophene, polyaniline, and polypyrrole.

The conductive polymer composition can be produced by ionic bonding of the vinyl sulfonic acid homopolymer or copolymer and the above-described conductive polymer, or by electropolymerization or chemical polymerization of the monomers forming the conductive polymer in the presence of the vinyl sulfonic acid homopolymer or copolymer.

The conductive polymer composition is film-formed and the film can also be used as a conductive polymer film. Examples of the film-forming method include casting method or spin coating method performed by dissolving in a suitable solvent, a melt method using a conductive polymer which melts, electropolymerization method, vacuum vapor deposition method, plasma polymerization method, Langmuir-Blodgett method, and molecular self-assembly method.

The conductive polymer composition or film obtained therefrom can be used in various optoelectronic part applications, such as a polymer light-emitting diode, an organic photovoltaic generation, a secondary battery, a conductive polymer sensor, a thin-film transistor device, an electroluminescent device, and an electrolytic capacitor.

Advantages of the Invention

The vinyl sulfonic acid according to the present invention has a high double bond content and a low metal content. According to the present invention, a vinyl sulfonic acid can be obtained which has little discoloration, hardly any change in color over time, and high quality.

Further, the vinyl sulfonic acid homopolymer and copolymer according to the present invention obtained using this vinyl sulfonic acid for a monomer have almost no impurities, a low metal content, and excellent quality.

Due to having such excellent properties, the vinyl sulfonic acid, homopolymer, and copolymer according to the present invention have sufficient durability even in a harsh environment of a high temperature and strong oxidizing atmosphere. Therefore, the vinyl sulfonic acid, homopolymer, and copolymer according to the present invention can be preferably used for an electric/electronic material, such as for a fuel cell electrolyte membrane, a photoresist composition, and a conductive polymer, or as a raw material thereof.

Further, the present invention provides a thin-film distillation apparatus suited to the production of a high-quality vinyl sulfonic acid. If purified using the apparatus according to the present invention, a vinyl sulfonic acid having a high double bond content and a low metal content can be obtained. In addition, according to the present invention, large-scale production of a high-quality vinyl sulfonic acid can be achieved by continuous operation of the thin-film distillation apparatus.

Thus, the present invention enables industrial production of a high-quality vinyl sulfonic acid.

DESCRIPTION OF THE REFERENCE NUMERALS

Figure 1:
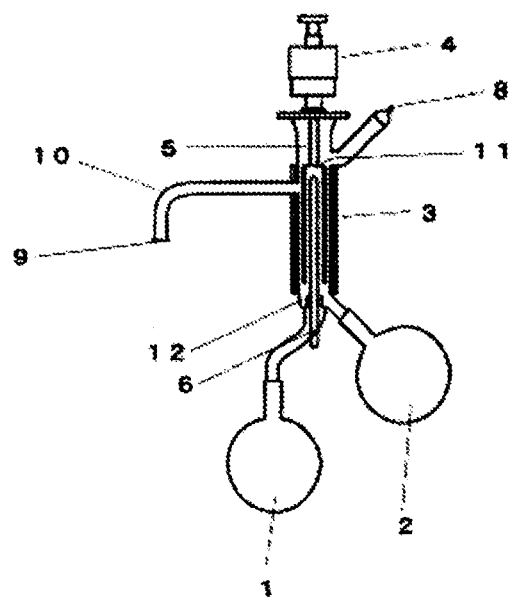
FIG. 1 shows a schematic diagram illustrating a configuration of the thin-film distillation apparatus used in Example II-1 of the present invention.

1 Vinyl sulfonic acid receiver, made from glass (Pyrex (registered trademark))
2 Residue receiver, made from glass (Pyrex (registered trademark))
3 Heater
4 Stirring drive member (stirring motor)
5 Stirring rotation member, made from tantalum
6 Cooling member, made from glass (Pyrex (registered trademark))
7 Stirring seal member, made from fluororesin (Teflon (registered trademark))
8 Vinyl sulfonic acid composition introduction port
9 Vacuum pump suction port
10 Distillation tower, made from glass (Pyrex (registered trademark))
11 Wiper member, configured from a section made from tantalum and a section made from fluororesin (Teflon (registered trademark))
12 Wall face for recovery of product trickling down the tower wall, made from glass (Pyrex (registered trademark))
13 Vinyl sulfonic acid vapor outlet

BEST MODE FOR CARRYING OUT THE INVENTION

Examples and Comparative Examples will now be illustrated to describe the present invention in more detail. However, the present invention is not limited to these.
Materials and Measurement Methods
Sodium vinyl sulfonate was used as the vinyl sulfonate serving as the raw material.

Measurement of the metal content was carried out by quantifying the amount based on an internal standard method using an ICP mass spectrometry apparatus (model: X Series X7 ICP-MS, manufactured by Thermo Fischer Scientific Inc.), and subtracting an operation blank value which had been simultaneously quantified to determine the content.

Acid value and iodine value measurement was carried out based on Japanese Industrial Standards JIS K0070-1992. The acid value was measured by neutralization titration.

The double bond content was calculated from the following formula based on the measured iodine value.

Double bond content(wt. %)=(iodine value)×(108.1/2)/126.9 wherein 108.1 is the molecular weight of vinyl sulfonic acid, and 126.9 is the atomic weight of iodine.

The metal removal rate (sodium removal rate) was determined from the following formula based on the measured acid value.

Metal removal rate(%)={(acid value after metal removal treatment)/(acid value before metal removal treatment)}×100.

The production step yield was calculated from the following formula based on the measured iodine value.

Yield(%)={(iodine value after metal removal treatment)/(iodine value before metal removal treatment)}×100.

The distillation recovery rate was calculated from the following formula based on the measured iodine value.

Recovery rate(%)={(iodine value after distillation)/(iodine value before distillation)}×100.

The weight average molecular weight of the copolymer was measured under the following condition A or condition B.
Condition A: Measured by size-exclusion chromatography (SEC) using a 0.2 M aqueous solution of sodium nitrate for a solvent and polyethylene oxide as a standard sample. Three columns manufactured by Tosoh Corporation, SEC columns TSK-Gel α-2500, α-3000, and α-4000, connected together were used for the column.
Condition B: Measured by size-exclusion chromatography (SEC) using a 0.1 wt. % solution of lithium bromide/N,N-dimethylformamide for a solvent and polystyrene oxide as a standard sample. Three columns manufactured by Showa Denko K.K., GPC columns KF-803, KF-804, and KF-805, connected together were used for the column.

Light absorbance was measured at a wavelength of 248 or 365 nm using a UV-visible spectrophotometer (UV-2450, manufactured by Shimadzu Corporation) by placing a measurement sample in a quartz cell having an optical path length of 1 cm.

Simultaneous thermogravimetric/differential thermal analysis (TG-DTA) was performed at a temperature range of 30 to 450° C. at a rate of temperature increase of 10° C./minute under a nitrogen atmosphere using the TG 8120 manufactured by Rigaku. Further, the point at which the weight had decreased by 10% from the start time in this measurement was taken as the 10% thermal decomposition temperature ($Td_{10\%}$).

In addition, unless stated otherwise, "%" in the respective examples represents "mole %" and "yield" indicates "molar yield".

COMPARATIVE EXAMPLE I-1

Sodium Removal Treatment Using Hydrochloric Acid and Batch Distillation 7.5 kg of a 25% aqueous solution of sodium vinyl sulfonate (N-SVS-25, manufactured by Asahi Kasei Fine Chemicals Co., Ltd.) was charged with 3 kg of 35% hydrochloric acid, and the resultant mixture was stirred at room temperature for 30 minutes. Next, under reduced pressure, about 4 L of water was evaporated. The precipitated salt was separated by filtration to perform a sodium removal treatment. This sodium removal treatment was carried out a further two times so that the sodiums in the sodium vinyl sulfonate were substituted with hydrogens, to thereby obtain an aqueous solution of vinyl sulfonic acid.

The sodium removal rate determined based on the acid value before the sodium removal treatment and the acid value after the three sodium removal treatments was 93.5%. Further, the yield determined from the iodine value before the sodium removal treatment and the iodine value after the three sodium removal treatments was 94.8%.

4.5 kg of the obtained aqueous solution of vinyl sulfonic acid was subjected to distillation under reduced pressure in a 5 L glass flask to obtain 2.1 kg of vinyl sulfonic acid. The recovery rate was 67%. The degree of vacuum was about 500 to 1,000 Pa. The fluctuations were large, and it was difficult to maintain the degree of vacuum. The obtained vinyl sulfonic acid had a double bond content of 98 wt. %, a Fe content of 750 ppb, a Na content of 5.7 ppm, a Ca content of 240 ppb, a Cr content of 330 ppb, and a Ni content of 220 ppb. Further, the vinyl sulfonic acid had a strong dark purple color from the time of extraction. In addition, a black residue lacking any fluidity was produced.

COMPARATIVE EXAMPLE I-2

Sodium Removal Treatment Using Strongly-Acidic Ion-Exchange Resin and Batch Concentration A column tower having an internal diameter of 200 mm and a height of 900 mm was filled with 26 L of a strongly-acidic ion-exchange resin (DOWEX (registered trademark) Monosphere 650C) which had been regenerated with hydrochloric acid in advance. A sodium removal treatment was carried out by flowing 12.2 kg of a 25 wt. % aqueous solution of sodium vinyl sulfonate (N-SVS-25, manufactured by Asahi Kasei Fine Chemicals Co., Ltd.) in from the bottom of the column, and then washing from the bottom of the column with 100 kg of ion-exchanged water. The sodium removal rate determined based on the acid value before and after the one-time sodium removal treatment was 98.4%. Further, the yield was 94.3%.

0.6 kg of dilute vinyl sulfonic acid composition obtained by this sodium removal treatment was concentrated under reduced pressure. As a result, a vinyl sulfonic acid was obtained which had a double bond content of 75 wt. %, a Fe content of 1,000 ppb, a Na content of 0.11 wt. %, a Ca content of 430 ppb, a Cr content of 130 ppb, and a Ni content of 24 ppb.

EXAMPLE I-1

Sodium Removal Treatment Using Strongly-Acidic Ion-Exchange Resin and Thin-Film Distillation A column tower having an internal diameter of 200 mm and a height of 900 mm was filled with 26 L of a strongly-acidic ion-exchange resin (DOWEX (registered trademark) Monosphere 650C) which had been regenerated with hydrochloric acid in advance. A sodium removal treatment was carried out by flowing 12.2 kg of a 25 wt. % aqueous solution of sodium vinyl sulfonate (N-SVS-25, manufactured by Asahi Kasei Fine Chemicals Co., Ltd.) in from the bottom of the column, and then washing from the bottom of the column with 100 kg of ion-exchanged water. The sodium removal rate determined based on the acid value before and after the one-time sodium removal treatment was 98.4%. Further, the yield was 94.3%. 300 kg of dilute vinyl sulfonic acid composition obtained by this sodium removal treatment was concentrated under reduced pressure.

4.2 kg of the obtained vinyl sulfonic acid composition was continuously fed into a thin-film distillation apparatus to try and carry out continuous distillation under reduced pressure. The temperature conditions were 160 to 200° C. Consequently, the degree of vacuum was maintained at 70 Pa, and the distillation operation could be stably continued. Further, there was no odor of sulfurous acid gas, and the recovery rate was maintained at about 94%.

The obtained vinyl sulfonic acid had a double bond content of 97.5 wt. %, a Fe content of 455 ppb, a Na content of 465 ppb, a Ca content of 50 ppb, and a Cr content of 120 ppb. The vinyl sulfonic acid had a pale yellow color when extracted, and no progression in color was seen even after 6 months had passed. Further, although a residue was produced during distillation, this residue had fluidity and a blackish brown color, and was easily cleaned.

EXAMPLE I-2

Sodium Removal Treatment Using Strongly-Acidic Ion-Exchange Resin and Thin-Film Distillation A column tower having an internal diameter of 200 mm and a height of 900 mm was filled with 26 L of a strongly-acidic ion-exchange resin (DOWEX (registered trademark) Monosphere 650C) which had been regenerated with hydrochloric acid in advance. A sodium removal treatment was carried out by flowing 12.2 kg of a 25 wt. % aqueous solution of sodium vinyl sulfonate (N-SVS-25, manufactured by Asahi Kasei Fine Chemicals Co., Ltd.) in from the bottom of the column, and then washing from the bottom of the column with 100 kg of ion-exchanged water. The sodium removal rate determined based on the acid value before and after the one-time sodium removal treatment was 96.5%. Further, the yield was 97.0%. 300 kg of dilute vinyl sulfonic acid composition obtained by this sodium removal treatment was concentrated under reduced pressure.

5.2 kg of the obtained vinyl sulfonic acid composition was continuously fed into a thin-film distillation apparatus to try and carry out continuous distillation under reduced pressure. The temperature conditions were 180 to 220° C. Consequently, the degree of vacuum was maintained at 70 to 90 Pa, and the distillation operation could be stably continued. Further, there was no odor of sulfurous acid gas, and the recovery rate was maintained at about 90%.

The obtained vinyl sulfonic acid had a double bond content of 96 wt. %, a Fe content of 730 ppb, a Na content of 220 ppb, a Ca content of 130 ppb, a Cr content of 155 ppb, and a Ni content of 145 ppb. The vinyl sulfonic acid had a pale yellow color when extracted, and no progression in color was seen even after 6 months had passed. Further, although a residue was produced during distillation, this residue had fluidity and a blackish brown color, and was easily cleaned.

EXAMPLE I-3

Sodium Removal Treatment Using Strongly-Acidic Ion-Exchange Resin and Thin-Film Distillation A column tower having an internal diameter of 200 mm and a height of 900 mm was filled with 26 L of a strongly-acidic ion-exchange resin (DOWEX (registered trademark) Monosphere 650C) which had been regenerated with hydrochloric acid in advance. A sodium removal treatment was carried out by flowing 12.2 kg of a 25 wt. % aqueous solution of sodium vinyl sulfonate (N-SVS-25, manufactured by Asahi Kasei Fine Chemicals Co., Ltd.) in from the bottom of the column, and then washing from the bottom of the column with 100 kg of ion-exchanged water. The sodium removal rate determined based on the acid value before and after the one-time sodium removal treatment was 96.8%. Further, the yield was 95.3%. 400 kg of dilute vinyl sulfonic acid composition obtained by this sodium removal treatment was concentrated under reduced pressure.

8.3 kg of the obtained vinyl sulfonic acid composition was continuously fed into a thin-film distillation apparatus to try and carry out continuous distillation under reduced pressure. The temperature conditions were 170 to 190° C. Consequently, the degree of vacuum was maintained at 55 to 100 Pa, and the distillation operation could be stably continued. Further, there was no odor of sulfurous acid gas, and the recovery rate was maintained at about 73%.

The obtained vinyl sulfonic acid had a double bond content of 97 wt. %, a Fe content of 44 ppb, a Na content of 35 ppb, a Ca content of 160 ppb, a Cr content of 9 ppb, and a Ni content of 6 ppb. The vinyl sulfonic acid had a pale yellow color when extracted, and no progression in color was seen even after 6 months had passed. Further, although a residue was produced during distillation, this residue had fluidity and a blackish brown color, and was easily cleaned.

EXAMPLE I-4

Sodium Removal Treatment Using Strongly-Acidic Ion-Exchange Resin and Thin-Film Distillation A column tower having an internal diameter of 200 mm and a height of 900 mm was filled with 26 L of a strongly-acidic ion-exchange resin (DOWEX (registered trademark) Monosphere 650C) which had been regenerated with hydrochloric acid in advance. A sodium removal treatment was carried out by flowing 12.2 kg of a 25 wt. % aqueous solution of sodium vinyl sulfonate (N-SVS-25, manufactured by Asahi Kasei Fine Chemicals Co., Ltd.) in from the bottom of the column, and then washing from the bottom of the column with 100 kg of ion-exchanged water. The sodium removal rate determined based on the acid value before and after the one-time sodium removal treatment was 96.8%. Further, the yield was 95.3%. 300 kg of dilute vinyl sulfonic acid composition obtained by this sodium removal treatment was concentrated under reduced pressure.

3.5 kg of the obtained vinyl sulfonic acid composition was continuously fed into a thin-film distillation apparatus to try and carry out continuous distillation under reduced pressure. The temperature conditions were 190 to 200° C. Consequently, the degree of vacuum was maintained at 65 to 130 Pa, and the distillation operation could be stably continued. Further, there was no odor of sulfurous acid gas, and the recovery rate was maintained at about 14%.

The obtained vinyl sulfonic acid had a high purity with a double bond content of 97 wt. %, and had a pale yellow color when extracted.

The residue produced during this distillation was subjected to continuous distillation under reduced pressure using a thin-film distillation apparatus under the same conditions as described above. Consequently, a recovery rate of about 17% was obtained. Further, the obtained vinyl sulfonic acid had a high purity with a double bond content of 98 wt. %, and had a pale yellow color when extracted.

The residue produced during this distillation was again subjected to continuous distillation under reduced pressure using a thin-film distillation apparatus under the same conditions as described above. This operation was repeated in the same manner 5 times.

The vinyl sulfonic acids obtained from these 5 operations all had a double bond content of 99 wt. %, a Fe, Na, Ca, Cr, and Ni content of less than 1 ppm, respectively, and a pale yellow color when extracted. Further, although a residue was produced during distillation, this residue had fluidity and a blackish brown color, and was easily cleaned.

EXAMPLE I-5

Sodium Removal Treatment Using Strongly-Acidic Ion-Exchange Resin and Thin-Film Distillation A column tower having an internal diameter of 200 mm and a height of 900 mm was filled with 26 L of a strongly-acidic ion-exchange resin (DOWEX (registered trademark) Monosphere 650C) which had been regenerated with hydrochloric acid in advance. A sodium removal treatment was carried out by flowing 12.2 kg of a 25 wt. % aqueous solution of sodium vinyl sulfonate (N-SVS-25, manufactured by Asahi Kasei Fine Chemicals Co., Ltd.) in from the bottom of the column, and then washing from the bottom of the column with 100 kg of ion-exchanged water. The sodium removal rate determined based on the acid value before and after the one-time sodium removal treatment was 99%. Further, the yield was 90%. 300 kg of dilute vinyl sulfonic acid composition obtained by this sodium removal treatment was concentrated under reduced pressure.

5.2 kg of the obtained vinyl sulfonic acid composition was continuously fed into a thin-film distillation apparatus to try and carry out continuous distillation under reduced pressure. The temperature conditions were 209 to 221° C. Consequently, the degree of vacuum was maintained at 15 to 25 Pa, and the distillation operation could be stably continued. Further, there was no odor of sulfurous acid gas, and the recovery rate was maintained at about 90%.

The obtained vinyl sulfonic acid had a double bond content of 97.2 wt. %, a Fe content of 415 ppb, a Na content of 62 ppb, a Cr content of 141 ppb, and a Ni content of 113 ppb. The vinyl sulfonic acid had a pale yellow color when extracted, and no progression in color was seen even after 6 months had passed. Further, although a residue was produced during distillation, this residue had fluidity and a blackish brown color, and was easily cleaned.

EXAMPLE I-6

Polymerization of Vinyl Sulfonic Acid by UV-Ray Irradiation

In a 20 mL sample bottle, 2 g of the vinyl sulfonic acid obtained in Example I-3 and 1 g (0.74 moles based on 1 mole of the vinyl sulfonic acid) of N,N-dimethylformamide (reagent grade, manufactured by Katayama Chemical Ltd.) were mixed. The resultant mixture was then irradiated with 360 nm UV-rays using a UV irradiation apparatus. After performing polymerization for 1 hour at a polymerization temperature of 35 to 45° C., a transparent resin-like solid was formed in the system.

The obtained polymer product was dissolved in ion-exchanged water, and then the resultant aqueous solution was added dropwise to a 20-fold weight of tetrahydrofuran. The resultant precipitate was filtrated and dissolved in ion-exchanged water. Then, the resultant aqueous solution was again added dropwise to a 20-fold weight of tetrahydrofuran. The produced precipitate was filtrated, and heated and dried under vacuum for one day and night at 50° C. to obtain a polymer.

The obtained polymer was a transparent solid with a pale yellow color. When measured by size-exclusion chromatography (hereinafter, "SEC") (condition A), the polymer product had a weight average molecular weight of $5.0 \times 10^4$.

EXAMPLE I-7

Radical Polymerization of Vinyl Sulfonic Acid

In a polymerization tube, 10 g of the vinyl sulfonic acid obtained in Example I-3 and 10 g of ion-exchanged water were mixed. The resultant mixture was charged with 0.2 g of azobisisobutyronitrile. The mixture was charged into a thoroughly evacuated sealed tube, and polymerized in a dark location at 60° C.

The obtained polymer product was dissolved in ion-exchanged water, and then the resultant aqueous solution was added dropwise to a 20-fold weight of tetrahydrofuran. The resultant precipitate was filtrated and dissolved in ion-exchanged water. Then, the resultant aqueous solution was again added dropwise to a 20-fold weight of tetrahydrofuran. The produced precipitate was filtrated, and heated and dried under vacuum for one day and night at 50° C. to obtain a polymer.

The obtained polymer was a transparent solid with a pale yellow color. When measured by SEC (condition A), the polymer product had a weight average molecular weight of $3.3 \times 10^4$.

COMPARATIVE EXAMPLE II-1

Sodium Removal Treatment Using Hydrochloric Acid 7.5 kg of a 25% aqueous solution of sodium vinyl sulfonate (N-SVS-25, manufactured by Asahi Kasei Fine Chemicals Co., Ltd.) was charged with 3 kg of 35% hydrochloric acid, and the resultant mixture was stirred at room temperature for 30 minutes. Next, under reduced pressure, about 4 L of water was evaporated. The precipitated salt was separated by filtration to perform a sodium removal treatment. This sodium removal treatment was carried out a further two times so that the sodiums in the sodium vinyl sulfonate were substituted with hydrogens, to thereby obtain an aqueous solution of vinyl sulfonic acid.

The sodium removal rate determined based on the acid value before the sodium removal treatment and the acid value after the three sodium removal treatments was 93.5%. Further, the yield determined from the iodine value before the sodium removal treatment and the iodine value after the three sodium removal treatments was 94.8%.

4.5 kg of the obtained aqueous solution of vinyl sulfonic acid was subjected to distillation under reduced pressure in a 5 L glass flask to obtain 2.1 kg of vinyl sulfonic acid. The recovery rate was 67%. The degree of vacuum was about 500 to 1,000 Pa. The fluctuations were large, and it was difficult to maintain the degree of vacuum. The obtained vinyl sulfonic acid had a double bond content of 98 wt. %, a Fe content of 750 ppb, a Na content of 5.7 ppm, a Ca content of 240 ppb, a Cr content of 330 ppb, and a Ni content of 220 ppb. Further, the vinyl sulfonic acid had a strong dark purple color from the time of extraction. In addition, a black residue lacking any fluidity was produced.

COMPARATIVE EXAMPLE II-2

Sodium Removal Treatment Using Strongly-Acidic Ion-Exchange Resin and Batch Concentration A column tower having an internal diameter of 200 mm and a height of 900 mm was filled with 26 L of a strongly-acidic ion-exchange resin (DOWEX (registered trademark) Monosphere 650C) which had been regenerated with hydrochloric acid in advance. A sodium removal treatment was carried out by flowing 12.2 kg of a 25 wt. % aqueous solution of sodium vinyl sulfonate (N-SVS-25, manufactured by Asahi Kasei Fine Chemicals Co., Ltd.) in from the bottom of the column, and then washing from the bottom of the column with 100 kg of ion-exchanged water. The sodium removal rate determined based on the acid value before and after the one-time sodium removal treatment was 98.4%. Further, the yield was 94.3%.

0.6 kg of dilute vinyl sulfonic acid composition obtained by this sodium removal treatment was concentrated under reduced pressure. As a result, a vinyl sulfonic acid was obtained which had a double bond content of 75 wt. %, a Fe content of 1,000 ppb, a Na content of 0.11 wt. %, a Ca content of 430 ppb, a Cr content of 130 ppb, and a Ni content of 24 ppb.

COMPARATIVE EXAMPLE II-3

Sodium Removal Treatment Using Strongly-Acidic Ion-Exchange Resin and Thin-Film Distillation A column tower having an internal diameter of 200 mm and a height of 900 mm was filled with 26 L of a strongly-acidic ion-exchange resin (DOWEX (registered trademark) Monosphere 650C) which had been regenerated with hydrochloric acid in advance. A sodium removal treatment was carried out by flowing 12.2 kg of a 25 wt. % aqueous solution of sodium vinyl sulfonate (N-SVS-25, manufactured by Asahi Kasei Fine Chemicals Co., Ltd.) in from the bottom of the column, and then washing from the bottom of the column with 100 kg of ion-exchanged water. The sodium removal rate determined based on the acid value before and after the one-time sodium removal treatment was 98.4%. Further, the yield was 94.3%. 300 kg of dilute vinyl sulfonic acid composition obtained by this sodium removal treatment was concentrated under reduced pressure.

4.2 kg of the obtained vinyl sulfonic acid composition was continuously fed into a thin-film distillation apparatus to try and carry out continuous distillation under reduced pressure. The temperature conditions were 160 to 200° C. Consequently, the degree of vacuum was maintained at 70 Pa, and the distillation operation could be stably continued. Further, there was no odor of sulfurous acid gas, and the recovery rate was maintained at about 94%.

The obtained vinyl sulfonic acid had a double bond content of 97.5 wt. %, a Fe content of 455 ppb, a Na content of 465 ppb, a Ca content of 50 ppb, and a Cr content of 120 ppb. The vinyl sulfonic acid had a pale yellow color when extracted, and no progression in color was seen even after 6 months had passed. Further, although a residue was produced during distillation, this residue had fluidity and a blackish brown color, and was easily cleaned.

EXAMPLE II-1

Sodium Removal Treatment Using Strongly-Acidic Ion-Exchange Resin and Thin-Film Distillation A column tower having an internal diameter of 200 mm and a height of 900 mm was filled with 26 L of a strongly-acidic ion-exchange resin (DOWEX (registered trademark) Monosphere 650C) which had been regenerated with hydrochloric acid in advance. A sodium removal treatment was carried out by flowing 12.2 kg of a 25 wt. % aqueous solution of sodium vinyl sulfonate (N-SVS-25, manufactured by Asahi Kasei Fine Chemicals Co., Ltd.) in from the bottom of the column, and then washing from the bottom of the column with 100 kg of ion-exchanged water. The sodium removal rate determined based on the acid value before and after the one-time sodium removal treatment was 98.4%. Further, the yield was 94.3%. 300 kg of dilute vinyl sulfonic acid composition obtained by this sodium removal treatment was concentrated under reduced pressure.

Using the thin-film distillation apparatus illustrated in FIG. 1, 3.6 kg of the obtained vinyl sulfonic acid composition was continuously fed into the apparatus to try and carry out continuous distillation under reduced pressure. The temperature conditions were 160 to 200° C. Consequently, the degree of vacuum was maintained at 70 Pa, and the distillation operation could be stably continued. Further, there was no odor of sulfurous acid gas, and the recovery rate was maintained at about 96%.

The obtained vinyl sulfonic acid had a high purity with a double bond content of 97 wt. %, a Fe content of 24 ppb, a Na content of 25 ppb, a Ca content of 30 ppb, a Cr content of 5 ppb, and a Ni content of 4 ppb. The vinyl sulfonic acid had a pale yellow color when extracted, and no progression in color was seen even after 6 months had passed. Further, although a residue was produced during distillation, this residue had fluidity and a blackish brown color, and was easily cleaned.

Further, concerning tantalum, a corrosion test was carried out by dipping the test piece in 165° C. vinyl sulfonic acid based on the method described in Chemical Apparatus Handbook (edited by the Society for Chemical Engineers, Japan, published by Maruzen, 1970, p. 500) item a, and measuring the weight change and change in appearance after 19 hours. The results showed that the rate of corrosion was 0.05 mm/year or less.

EXAMPLE II-2

Sodium Removal Treatment Using Strongly-Acidic Ion-Exchange Resin and Thin-Film Distillation A column tower having an internal diameter of 200 mm and a height of 900 mm was filled with 26 L of a strongly-acidic ion-exchange resin (DOWEX (registered trademark) Monosphere 650C) which had been regenerated with hydrochloric acid in advance. A sodium removal treatment was carried out by flowing 12.2 kg of a 25 wt. % aqueous solution of sodium vinyl sulfonate (N-SVS-25, manufactured by Asahi Kasei Fine Chemicals Co., Ltd.) in from the bottom of the column, and then washing from the bottom of the column with 100 kg of ion-exchanged water. The sodium removal rate determined based on the acid value before and after the one-time sodium removal treatment was 98.4%. Further, the yield was 94.3%. 300 kg of dilute vinyl sulfonic acid composition obtained by this sodium removal treatment was concentrated under reduced pressure.

Figure 2:
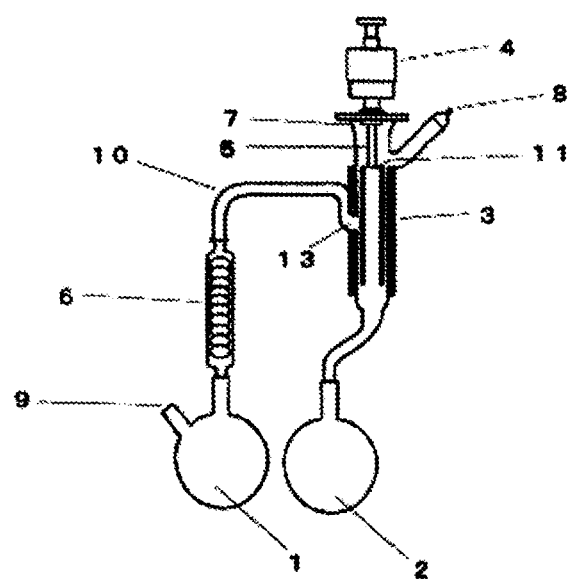
FIG. 2 shows a schematic diagram illustrating a configuration of the thin-film distillation apparatus used in Examples II-2 to II-4 of the present invention.

Using the thin-film distillation apparatus illustrated in FIG. 2, 3.6 kg of the obtained vinyl sulfonic acid composition was continuously fed into the apparatus to try and carry out continuous distillation under reduced pressure. The temperature conditions were 160 to 200° C. Consequently, the degree of vacuum was maintained at 70 Pa, and the distillation operation could be stably continued. Further, there was no odor of sulfurous acid gas, and the recovery rate was maintained at about 96%.

The obtained vinyl sulfonic acid had a high purity with a double bond content of 97 wt. %, a Fe content of 7 ppb, a Na content of 25 ppb, a Ca content of less than 20 ppb, a Cr content of less than 1 ppb, and a Ni content of less than 1 ppb. The vinyl sulfonic acid had a pale yellow color when extracted, and no progression in color was seen even after 6 months had passed. Further, although a residue was produced during distillation, this residue had fluidity and a blackish brown color, and was easily cleaned.

EXAMPLE II-3

Sodium Removal Treatment Using Strongly-Acidic Ion-Exchange Resin and Thin-Film Distillation A column tower having an internal diameter of 200 mm and a height of 900 mm was filled with 26 L of a strongly-acidic ion-exchange resin (DOWEX (registered trademark) Monosphere 650C) which had been regenerated with hydrochloric acid in advance. A sodium removal treatment was carried out by flowing 12.2 kg of a 25 wt. % aqueous solution of sodium vinyl sulfonate (N-SVS-25, manufactured by Asahi Kasei Fine Chemicals Co., Ltd.) in from the bottom of the column, and then washing from the bottom of the column with 100 kg of ion-exchanged water. The sodium removal rate determined based on the acid value before and after the one-time sodium removal treatment was 96.8%. Further, the yield was 95.3%. 300 kg of dilute vinyl sulfonic acid composition obtained by this sodium removal treatment was concentrated under reduced pressure.

Using the thin-film distillation apparatus illustrated in FIG. 2, 3.5 kg of the obtained vinyl sulfonic acid composition was continuously fed into the apparatus to try and carry out continuous distillation under reduced pressure. The temperature conditions were 190 to 200° C. Consequently, the degree of vacuum was maintained at 65 to 130 Pa, and the distillation operation could be stably continued. Further, there was no odor of sulfurous acid gas, and the recovery rate was maintained at about 14%.

The obtained vinyl sulfonic acid had a high purity, with a double bond content of 97 wt. %, and had a pale yellow color when extracted.

The residue produced during this distillation was subjected to continuous distillation under reduced pressure using a thin-film distillation apparatus under the same conditions as described above. Consequently, a recovery rate of about 17% was obtained. Further, the obtained vinyl sulfonic acid had a high purity with a double bond content of 98 wt. %, and had a pale yellow color when extracted.

The residue produced during this distillation was again subjected to continuous distillation under reduced pressure using a thin-film distillation apparatus under the same conditions as described above. This operation was repeated in the same manner 5 times.

The vinyl sulfonic acids obtained from these 5 operations all had a high purity with a double bond content of 99 wt. %, a Fe content of 10 to 15 ppb, a Na content of less than 10 ppb, a Ca content of less than 20 ppb, a Cr content of less than 1 ppb, and a Ni content of less than 1 ppb, and a pale yellow color when extracted. Further, although a residue was produced during distillation, this residue had fluidity and a blackish brown color, and was easily cleaned.

TEST EXAMPLE 1

The measurement results of the light absorbance of the vinyl sulfonic acids obtained in Example I-2 and Example II-2 at 248 nm and 365 nm are shown in Table 1.

TABLE 1

|  | 248 nm | 365 nm |
| --- | --- | --- |
| Example I-2 | 0.97 | 0.24 |
| Example II-2 | 0.72 | 0.08 |

As shown in Table 1, the vinyl sulfonic acids obtained in Example I-2 and Example II-2 both had a small light absorbance. Especially, it can be seen that the vinyl sulfonic acid obtained in Example II-2 had a smaller light absorbance, specifically, a larger transmittance.

Based on these results, it is predicted that if this vinyl sulfonic acid having a lower metal content is used in a photoresist composition, the light transmittance during exposure would be high, and that a resist pattern of a photoresist film formed after developing could be formed with a stable line width.

EXAMPLE II-4

Sodium Removal Treatment Using Strongly-Acidic Ion-Exchange Resin and Thin-Film Distillation A column tower having an internal diameter of 200 mm and a height of 900 mm was filled with 26 L of a strongly-acidic ion-exchange resin (DOWEX (registered trademark) Monosphere 650C) which had been regenerated with hydrochloric acid in advance. A sodium removal treatment was carried out by flowing 12.2 kg of a 25 wt. % aqueous solution of sodium vinyl sulfonate (N-SVS-25, manufactured by Asahi Kasei Fine Chemicals Co., Ltd.) in from the bottom of the column, and then washing from the bottom of the column with 100 kg of ion-exchanged water. The sodium removal rate determined based on the acid value before and after the one-time sodium removal treatment was 99%. Further, the yield was 88.4%. 300 kg of dilute vinyl sulfonic acid composition obtained by this sodium removal treatment was concentrated under reduced pressure.

Using the thin-film distillation apparatus illustrated in FIG. 2, 15.4 kg of the obtained vinyl sulfonic acid composition was continuously fed into the apparatus to try and carry out continuous distillation under reduced pressure. The temperature conditions were 185 to 200° C. Consequently, the degree of vacuum was maintained at 100 to 150 Pa, and the distillation operation could be stably continued. Further, there was no odor of sulfurous acid gas, and the recovery rate was maintained at about 80%.

The obtained vinyl sulfonic acid had a high purity with a double bond content of 98.1 wt. %, a Fe content of 1.5 ppb, a Na content of 10 ppb, a Ca content of less than 20 ppb, a Cr content of less than 1 ppb. The vinyl sulfonic acid had a pale yellow color when extracted, and no progression in color was seen even after 6 months had passed. Further, although a residue was produced during distillation, this residue had fluidity and a blackish brown color, and was easily cleaned.

EXAMPLE II-5

Polymerization of Vinyl Sulfonic Acid by UV-Ray Irradiation

In a 20 mL sample bottle, 2 g of the vinyl sulfonic acid obtained in Example II-2 and 1 g (0.74 moles based on 1 mole of the vinyl sulfonic acid) of N,N-dimethylformamide (reagent grade, manufactured by Katayama Chemical Ltd.) were mixed. The resultant mixture was then irradiated with 360 nm UV-rays using a UV irradiation apparatus. After performing polymerization for 1 hour at a polymerization temperature of 35 to 45° C., a transparent resin-like solid was formed in the system.

The obtained polymer product was dissolved in ion-exchanged water, and then the resultant aqueous solution was added dropwise to a 20-fold weight of tetrahydrofuran. The resultant precipitate was filtrated and dissolved in ion-exchanged water. Then, the resultant aqueous solution was again added dropwise to a 20-fold weight of tetrahydrofuran. The produced precipitate was filtrated, and heated and dried under vacuum for one day and night at 50° C. to obtain a polymer.

The obtained polymer was a transparent solid with a pale yellow color. When measured by SEC (condition A), the polymer product had a weight average molecular weight of $5.0 \times 10^4$.

EXAMPLE II-6

Radical Polymerization of Vinyl Sulfonic Acid

In a polymerization tube, 10 g of the vinyl sulfonic acid obtained in Example II-2 and 10 g of ion-exchanged water were mixed. The resultant mixture was charged with 0.2 g of azobisisobutyronitrile. The mixture was charged into a thoroughly evacuated sealed tube, and polymerized in a dark location at 60° C.

The obtained polymer product was dissolved in ion-exchanged water, and then the resultant aqueous solution was added dropwise to a 20-fold weight of tetrahydrofuran. The resultant precipitate was filtrated and dissolved in ion-exchanged water. Then, the resultant aqueous solution was again added dropwise to a 20-fold weight of tetrahydrofuran.

The produced precipitate was filtrated, and heated and dried under vacuum for one day and night at 50° C. to obtain a polymer.

The obtained polymer was a transparent solid with a pale yellow color. When measured by SEC (condition A), the polymer product had a weight average molecular weight of $3.3 \times 10^4$.

COMPARATIVE EXAMPLE II-4

Sodium Polyvinyl Sulfonate

The molecular weight of sodium polyvinyl sulfonate (manufactured by Aldrich) was measured. Also, the thermal property of this sodium polyvinyl sulfonate was evaluated. When measured by SEC (condition A), the sodium polyvinyl sulfonate had a weight average molecular weight of $9.0 \times 10^4$.

TEST EXAMPLE 2

The measurement results of simultaneous thermogravimetric/differential thermal analysis (TG-DTA) for the polymers obtained in Examples I-7 and II-5 and the polymer of Comparative Example II-4 are shown in Table 2. In Table 2, $Td_{10\%}$ represents the 10% thermal decomposition temperature.

TABLE 2

|  | $Td_{10\%}$ |
|---|---|
| Example I-7 | 156° C. |
| Example II-5 | 187° C. |
| Comparative Example II-4 | 355° C. |

As shown in Table 2, it can be seen that the polymers obtained using the vinyl sulfonic acid according to the present invention had a $Td_{10\%}$ of 150° C. or more.

Since the sodium polyvinyl sulfonate of Comparative Example II-4 was in the form of a sodium salt of a sulfonic acid group, it can be understood that it had excellent thermal stability. However, since sodium polyvinyl sulfonate is a metal salt, it is soluble in water, and thus ionizes in the presence of water. Therefore, such a sodium polyvinyl sulfonate is not suitable for a fuel cell membrane.

Vinyl sulfonic acid has a structure which is formed only from a vinyl group and a sulfonic acid group. Therefore, a polymer formed from sulfonic acid as a monomer has a much higher density of sulfonic acid groups than a polymer formed using another sulfonic-acid-group-containing vinyl monomer.

Further, a polymer obtained using the vinyl sulfonic acid according to the present invention has a low level of impurities, and a low metal content, so that the sulfonic acid group density is increased.

In addition, as shown by the results in Table 2, the polymer obtained using the vinyl sulfonic acid according to the present invention also had excellent thermal stability. Therefore, it is predicted that this polymer would be sufficiently stable from room temperature to about 120° C., which is the typical operation temperature of a solid polymer fuel cell.

Moreover, the polymer according to the present invention can be obtained using a vinyl sulfonic acid having a low metal content. Therefore, it is predicted that the metal content can be decreased, and the oxidation resistance of the polymer electrolyte membrane can be improved.

Consequently, it is considered that the polyvinyl sulfonic acid polymer according to the present invention can be used as an excellent material for an excellent polymer electrolyte membrane for a fuel cell.

TEST EXAMPLE 3

PEDOT/PVS Chemical Oxidation Polymerization and Electrical Conductivity Thereof

In an aqueous solution of polyvinyl sulfonic acid (hereinafter, "PVS"), 3,4-ethylenedioxythiophene was subjected to chemical oxidation polymerization to produce a conductive polymer composition PEDOT/PVS comprised poly(3,4-ethylenedioxythiophene) (hereinafter, "PEDOT") and polyvinyl sulfonic acid (PVS).

A 100 mL pear-shaped flask was charged with 0.135 g of the vinyl sulfonic acid of Example 11-5, 50 mL of ion-exchanged water, and 0.71 g of 3,4-ethylenedioxythiophene, and the resultant mixture was stirred for 1 hour.

The mixture was charged with 1.14 g of ammonium persulfate. Then, the flask was thoroughly purged with nitrogen, and the mixture was polymerized at room temperature for 12 hours. After the polymerization reaction finished, the product underwent dialysis for 3 days with ion-exchanged water using a dialysis membrane having a molecular weight cutoff of 3,500 (Spectra/Por (registered trademark), manufactured by Spectrum) to remove the low molecular weight component.

The obtained PEDOT/PVS dispersion was cast onto a Teflon (registered trademark) substrate, and then heated and dried at 40° C. for one night. The electrical conductivity was measured at room temperature using a four-point probe tester (K-705RS, Kyowariken Co., Ltd.).

For comparison, the electrical conductivity of PEDOT/PSS (polystyrene sulfonic acid) (manufactured by Aldrich) was measured in the same manner. These results are shown in Table 3.

TABLE 3

|  |  | Electrical Conductivity (Scm$^{-1}$) |
|---|---|---|
| Example | PEDOT/PVS | $5.6 \times 10^{-3}$ |
| Comparative Example | PEDOT/PSS | $3.9 \times 10^{-3}$ |

As shown in Table 3, the PEDOT/PVS exhibited a higher electrical conductivity than the electrical conductivity of the PEDOT/PSS.

It is thought that PEDOT disperses in the water and PSS is a dopant, and PVS also functioning as a dopant similar to PSS.

Further, structurally, since PSS has an aromatic ring, it has a high glass transition point, and poor contact properties with the substrate. On the other hand, since PVS does not have an aromatic ring, PVS is expected to have a low glass transition point, and excellent contact properties with the substrate.

More specifically, it is thought that PVS can be used as a better conductive polymer dopant than PSS.

EXAMPLE III-1

Copolymerization of Vinyl Sulfonic Acid and Methyl Methacrylate by UV Irradiation A 4.5 mL quartz cell was charged with 0.5 g of the vinyl sulfonic acid obtained in Example I-1, 0.5 g of methyl methacrylate, and 0.5 g of N,N-dimethylformamide, and the resultant mixture was uniformly mixed. The methyl methacrylate was produced by charging methyl methacrylate (reagent, manufactured by Wako Pure Chemical Industries, Ltd.) into a four-neck flask made from Pyrex (registered trademark) glass, adding 0.1 wt. % hydroquinone monomethyl ether based on the methyl methacrylate, and carrying out distillation under reduced pressure to purify the product.

The obtained mixture was irradiated with UV-rays for 20 minutes. Subsequently, this reaction solution was added dropwise to a large amount methanol, and a white solid product was separated. The obtained white solid product was heated and dried under vacuum for one day and night at 50° C. to obtain a polymer. The obtained polymer was a white transparent solid. When measured by SEC (condition B), the polymer product had a weight average molecular weight of $1.1 \times 10^6$.

EXAMPLE III-2

Copolymerization of Vinyl Sulfonic Acid and Methyl Methacrylate by UV Irradiation A copolymer was obtained by carrying out polymerization in the same manner as in Example III-1, except that the weights of the vinyl sulfonic acid and the methyl methacrylate were changed to the values shown in Table 4.

EXAMPLE III-3

Copolymerization of Vinyl Sulfonic Acid and Methyl Methacrylate by UV Irradiation A copolymer was obtained by carrying out polymerization in the same manner as in Example III-1, except that the weights of the vinyl sulfonic acid and the methyl methacrylate were changed to the values shown in Table 4.

Table 4 shows the weight and mole % of the monomers used in Examples III-1 to III-3, and the weight average molecular weights of the obtained copolymers. In the below, the term "mole %" represents a ratio of a number of moles of each monomer when a number of moles of all the monomers constituting the copolymer is 100, based on the number of moles calculated from the weight (g) of the monomers.

TABLE 4

| | Monomer Composition | | | | Copolymer |
| | Weight (g) | | Mole % | | Weight |
| | Vinyl Sulfonic Acid | Methyl Methacrylate | Vinyl Sulfonic Acid | Methyl Methacrylate | Average Molecular Weight |
| --- | --- | --- | --- | --- | --- |
| Example III-1 | 0.50 | 0.50 | 48% | 52% | $1.1 \times 10^6$ |
| Example III-2 | 0.80 | 0.20 | 79% | 21% | $0.8 \times 10^6$ |
| Example III-3 | 0.20 | 0.80 | 19% | 81% | $1.3 \times 10^6$ |

EXAMPLE III-4

Radical Polymerization of Vinyl Sulfonic Acid and Acrylic Acid

A 50 mL pear-shaped flask was charged with 1.73 g of the vinyl sulfonic acid obtained Example I-1, 0.29 g of acrylic acid (reagent, manufactured by Wako Pure Chemical Industries, Ltd.), 44 mg of ammonium persulfate as an initiator, and 4 mL of ion-exchanged water as a reaction solvent. Here, the 44 mg of ammonium persulfate was equivalent to 1 mole % based on the total number of moles of the vinyl sulfonic acid and the acrylic acid.

The vinyl sulfonic acid, the acrylic acid and ammonium persulfate were dissolved. Then, the flask was thoroughly purged with nitrogen, and the mixture was stirred for 16 hours at 60° C. After cooling to room temperature, 15 mL of methanol was added. The mixture was then filtered and washed to remove the residual initiator.

The methanol filtrate was concentrated, then added dropwise to a large amount of tetrahydrofuran, whereby a white solid product was separated. The obtained white solid product was heated and dried under vacuum for two days at 60° C. to obtain a polymer.

The obtained polymer was soluble in water, methanol, N,N-dimethylformamide and the like. Further, when measured by SEC (condition B), the obtained polymer had a weight average molecular weight of $8 \times 10^4$.

EXAMPLE III-5

Radical Polymerization of Vinyl Sulfonic Acid and Acrylic Acid

A copolymer was obtained by carrying out polymerization in the same manner as in Example III-4, except that the weights of the vinyl sulfonic acid and the acrylic acid were changed to the values shown in Table 5.

EXAMPLE III-6

Radical Polymerization of Vinyl Sulfonic Acid and Acrylic Acid

A copolymer was obtained by carrying out polymerization in the same manner as in Example III-4, except that the weights of the vinyl sulfonic acid and the acrylic acid were changed to the values shown in Table 5.

Table 5 shows the weight and mole % of the monomers used in Examples III-4 to III-6, and the weight average molecular weights of the obtained copolymers.

TABLE 5

| | Monomer Composition | | | | Copolymer |
| | Weight (g) | | Mole % | | Weight |
| | Vinyl Sulfonic Acid | Acrylic Acid | Vinyl Sulfonic Acid | Acrylic Acid | Average Molecular Weight |
| --- | --- | --- | --- | --- | --- |
| Example III-4 | 1.73 | 0.29 | 80% | 20% | $0.8 \times 10^5$ |
| Example III-5 | 1.08 | 0.72 | 50% | 50% | $3.1 \times 10^5$ |
| Example III-6 | 0.43 | 1.15 | 20% | 80% | $1.2 \times 10^6$ |

EXAMPLE III-7

Copolymerization of Vinyl Sulfonic Acid and Acrylamide by UV Irradiation

A 4.5 mL quartz cell was charged with 0.5 g of the vinyl sulfonic acid obtained in Example I-1, 0.5 g of acrylamide (reagent, manufactured by Wako Pure Chemical Industries, Ltd.), and 0.5 g of N,N-dimethylformamide. The resultant mixture was uniformly mixed, and then subjected to UV irradiation for 20 minutes to obtain a polymer product.

The obtained polymer product was dissolved in ion-exchanged water, and then the resultant aqueous solution was added dropwise to a 20-fold weight of acetonitrile. The resultant precipitate was filtrated and dissolved in ion-exchanged water. Then, the resultant aqueous solution was again added dropwise to a 20-fold weight of acetonitrile. The produced precipitate was filtrated, and heated and dried under vacuum for one day and night at 50° C. to obtain a polymer. When measured by SEC (condition A), the polymer product had a weight average molecular weight of $4.0 \times 10^5$.

EXAMPLE III-8

Copolymerization of Vinyl Sulfonic Acid and Acrylamide by UV Irradiation

A copolymer was obtained by carrying out polymerization in the same manner as in Example III-7, except that the weights of the vinyl sulfonic acid and the acrylamide were changed to the values shown in Table 6.

EXAMPLE III-9

Copolymerization of Vinyl Sulfonic Acid and Acrylamide by UV Irradiation

A copolymer was obtained by carrying out polymerization in the same manner as in Example III-7, except that the weights of the vinyl sulfonic acid and the acrylamide were changed to the values shown in Table 6.

Table 6 shows the weight and mole % of the monomers used in Examples III-7 to III-9, and the weight average molecular weights of the obtained copolymers.

TABLE 6

| | Monomer Composition | | | | Copolymer |
|---|---|---|---|---|---|
| | Weight (g) | | Mole % | | Weight |
| | Vinyl Sulfonic Acid | Acrylamide | Vinyl Sulfonic Acid | Acrylamide | Average Molecular Weight |
| Example III-7 | 0.50 | 0.50 | 40% | 60% | $4.0 \times 10^5$ |
| Example III-8 | 0.67 | 0.33 | 57% | 43% | $5.6 \times 10^5$ |
| Example III-9 | 0.91 | 0.09 | 87% | 13% | $8.5 \times 10^4$ |

EXAMPLE III-10

Copolymerization of Vinyl Sulfonic Acid and Acrylonitrile by UV Irradiation

A 55 mm diameter dish was charged with 0.6 g of the vinyl sulfonic acid obtained in Example I-1, 2.0 g of acrylonitrile, 0.3 g of N,N-dimethylformamide, and 25 mg of azobisisobutyronitrile, and the resultant mixture was uniformly mixed. The acrylonitrile was produced by charging acrylonitrile (reagent, manufactured by Wako Pure Chemical Industries, Ltd.) into a four-neck flask made from Pyrex (registered trademark) glass, adding 0.1 wt. % hydroquinone monomethyl ether based on the acrylonitrile, and carrying out distillation under reduced pressure to purify the product. The N,N-dimethylformamide was produced by charging N,N-dimethylformamide (reagent, manufactured by Wako Pure Chemical Industries, Ltd.) into a four-neck flask made from Pyrex (registered trademark) glass, and carrying out distillation under reduced pressure to purify the product.

The mixture was irradiated with UV-rays for 25 minutes. Subsequently, the obtained polymer product was dissolved in N,N-dimethylformamide, and the resultant solution was added dropwise to a 20-fold weight of ion-exchanged water. The resultant precipitate was filtrated, and heated and dried under vacuum for one day and night at 50° C. to obtain a polymer.

The obtained polymer was a white transparent solid. When measured by SEC (condition B), the polymer product had a weight average molecular weight of $2.0 \times 10^6$.

EXAMPLE III-11

Copolymerization of Vinyl Sulfonic Acid and Acrylonitrile by UV Irradiation

A copolymer was obtained by carrying out polymerization in the same manner as in Example III-10, except that the weights of the vinyl sulfonic acid, the acrylonitrile, and the N,N-dimethylformamide were changed to the values shown in Table 7.

EXAMPLE III-12

Copolymerization of Vinyl Sulfonic Acid and Acrylonitrile by UV Irradiation

A copolymer was obtained by carrying out polymerization in the same manner as in Example III-10, except that the weights of the vinyl sulfonic acid, the acrylonitrile, and the N,N-dimethylformamide were changed to the values shown in Table 7.

Table 7 shows the weight and mole % of the monomers used in Examples III-10 to III-12, and the weight average molecular weights of the obtained copolymers.

TABLE 7

| | Monomer Composition | | | | | Copolymer |
|---|---|---|---|---|---|---|
| | Weight (g) | | Mole % | | | Weight |
| | Vinyl Sulfonic Acid | Acrylonitrile | Vinyl Sulfonic Acid | Acrylonitrile | DMF Weight (g) | Average Molecular Weight |
| Example III-10 | 0.6 | 2.0 | 13% | 87% | 0.3 | $2.0 \times 10^6$ |
| Example III-11 | 0.5 | 2.0 | 11% | 89% | 0.25 | $1.4 \times 10^6$ |
| Example III-12 | 0.4 | 2.0 | 9% | 91% | 0.2 | $1.4 \times 10^6$ |

As shown in Tables 4 to 7, it can be seen that the vinyl sulfonic acid copolymers having a sufficient weight average molecular weight were obtained using the vinyl sulfonic acid according to the present invention.

EXAMPLE III-13

Copolymerization of Vinyl Sulfonic Acid and Acrylonitrile by UV Irradiation

A 10 mm quartz cell was charged with 0.9 g of the vinyl sulfonic acid obtained in Example 1-5, 1.0 g of acrylonitrile, and 0.45 g of N,N-dimethylformamide, and the resultant mixture was uniformly mixed. The mixture was then irradiated with UV-rays for 40 minutes to obtain a polymer product. The acrylonitrile was produced by charging acrylonitrile (reagent, manufactured by Tokyo Chemical Industry Co., Ltd.) into a four-neck flask made from Pyrex (registered trademark) glass, and carrying out distillation under reduced pressure to purify the product. The N,N-dimethylformamide was produced by charging N,N-dimethylformamide (reagent, manufactured by Wako Pure Chemical Industries, Ltd.) into a four-neck flask made from Pyrex (registered trademark) glass, and carrying out distillation under reduced pressure to purify the product.

The obtained polymer product was dissolved in N,N-dimethylformamide, and then the resultant solution was added dropwise to a 20-fold weight of isopropyl alcohol. The resultant precipitate was filtered, and washed with 100 mL of isopropyl alcohol, and then heated and dried under vacuum for one day and night at 50° C. to obtain a 0.28 g of a polymer.

When measured by SEC (condition B), the obtained polymer product had a weight average molecular weight of $3.2 \times 10^6$. Further, the ratio of the vinyl sulfonic acid units in the polymer was measured by subjecting the polymer to ion-exchange with sodium chloride and then titrating with aqueous sodium hydroxide. The measurement value was 12.8 wt. %.

From the results of Example III-13, it was found that the acrylonitrile copolymer obtained using the vinyl sulfonic acid having a high purity and a low metal content was a polymer which comprised a large amount of vinyl sulfonic acid units and which had a high molecular weight.

The polymer comprised a large amount of vinyl sulfonic acid units, therefore it is thought that a polymer electrolyte membrane having excellent proton conductivity can be obtained by use of the polymer.

Further, it is thought that a vinyl sulfonic acid copolymer having a high molecular weight has good film-forming properties and can be used to produce a strong membrane.

EXAMPLE IV-1

Copolymerization of Vinyl Sulfonic Acid and Methyl Methacrylate by UV Irradiation A 4.5 mL quartz cell was charged with 0.5 g of the vinyl sulfonic acid obtained in Example II-1, 0.5 g of methyl methacrylate, and 0.5 g of N,N-dimethylformamide, and the resultant mixture was uniformly mixed. The methyl methacrylate was produced by charging methyl methacrylate (reagent, manufactured by Wako Pure Chemical Industries, Ltd.) into a four-neck flask made from Pyrex (registered trademark) glass, adding 0.1 wt. % hydroquinone monomethyl ether based on the methyl methacrylate, and carrying out distillation under reduced pressure to purify the product.

The obtained mixture was irradiated with UV-rays for 20 minutes. Subsequently, this reaction solution was added dropwise to a large amount methanol, and a white solid product was separated. The obtained white solid product was heated and dried under vacuum for one day and night at 50° C. to obtain a polymer.

The obtained polymer was a white transparent solid. When measured by SEC (condition B), the polymer had a weight average molecular weight of $1.1 \times 10^6$.

EXAMPLE IV-2

Copolymerization of Vinyl Sulfonic Acid and Methyl Methacrylate by UV Irradiation A copolymer was obtained by carrying out polymerization in the same manner as in Example IV-1, except that the weights of the vinyl sulfonic acid and the methyl methacrylate were changed to the values shown in Table 8.

EXAMPLE IV-3

Copolymerization of Vinyl Sulfonic Acid and Methyl Methacrylate by UV Irradiation A copolymer was obtained by carrying out polymerization in the same manner as in Example IV-1, except that the weights of the vinyl sulfonic acid and the methyl methacrylate were changed to the values shown in Table 8.

Table 8 shows the weight and mole % of the monomers used in Examples IV-1 to IV-3, and the weight average molecular weights of the obtained copolymers.

TABLE 8

| | Monomer Composition | | | | Copolymer Weight |
|---|---|---|---|---|---|
| | Weight (g) | | Mole % | | |
| | Vinyl Sulfonic Acid | Methyl Methacrylate | Vinyl Sulfonic Acid | Methyl Methacrylate | Average Molecular Weight |
| Example IV-1 | 0.50 | 0.50 | 48% | 52% | $1.1 \times 10^6$ |
| Example IV-2 | 0.80 | 0.20 | 79% | 21% | $0.8 \times 10^6$ |
| Example IV-3 | 0.20 | 0.80 | 19% | 81% | $1.3 \times 10^6$ |

EXAMPLE IV-4

Radical Polymerization of Vinyl Sulfonic Acid and Acrylic Acid

A 50 mL pear-shaped flask was charged with 1.73 g of the vinyl sulfonic acid obtained Example II-1, 0.29 g of acrylic acid (reagent, manufactured by Wako Pure Chemical Industries, Ltd.), 44 mg of ammonium persulfate as an initiator, and 4 mL of ion-exchanged water as a reaction solvent. Here, the 44 mg of ammonium persulfate was equivalent to 1 mole % based on the total number of moles of the vinyl sulfonic acid and the acrylic acid.

The vinyl sulfonic acid, the acrylic acid and the ammonium persulfate were dissolved. Then, the flask was thoroughly purged with nitrogen, and the mixture was stirred for 16 hours at 60° C. After cooling to room temperature, 15 mL of methanol was added. The mixture was then filtered and washed to remove the residual initiator.

The methanol filtrate was concentrated, then added dropwise to a large amount of tetrahydrofuran, whereby a white solid product was separated. The obtained white solid product was heated and dried under vacuum for two days at 60° C. to obtain a polymer.

The obtained polymer was soluble in water, methanol, N,N-dimethylformamide and the like. Further, when measured by SEC (condition B), the obtained polymer had a weight average molecular weight of $8 \times 10^4$.

EXAMPLE IV-5

Radical Polymerization of Vinyl Sulfonic Acid and Acrylic Acid

A copolymer was obtained by carrying out polymerization in the same manner as in Example IV-4, except that the weights of the vinyl sulfonic acid and the acrylic acid were changed to the values shown in Table 9.

EXAMPLE IV-6

Radical Polymerization of Vinyl Sulfonic Acid and Acrylic Acid

A copolymer was obtained by carrying out polymerization in the same manner as in Example IV-4, except that the weights of the vinyl sulfonic acid and the acrylic acid were changed to the values shown in Table 9.

Table 9 shows the weight and mole % of the monomers used in Examples IV-4 to IV-6, and the weight average molecular weights of the obtained copolymers.

TABLE 9

|  | Monomer Composition | | | | Copolymer |
| --- | --- | --- | --- | --- | --- |
|  | Weight (g) | | Mole % | | Weight |
|  | Vinyl Sulfonic Acid | Acrylic Acid | Vinyl Sulfonic Acid | Acrylic Acid | Average Molecular Weight |
| Example IV-4 | 1.73 | 0.29 | 80% | 20% | $0.8 \times 10^5$ |
| Example IV-5 | 1.08 | 0.72 | 50% | 50% | $3.1 \times 10^5$ |
| Example IV-6 | 0.43 | 1.15 | 20% | 80% | $1.2 \times 10^6$ |

EXAMPLE IV-7

Copolymerization of Vinyl Sulfonic Acid and Acrylamide by UV Irradiation

A 4.5 mL quartz cell was charged with 0.5 g of the vinyl sulfonic acid obtained in Example II-2, 0.5 g of acrylamide (reagent, manufactured by Wako Pure Chemical Industries, Ltd.), and 0.5 g of N,N-dimethylformamide. The resultant mixture was uniformly mixed, and then subjected to UV irradiation for 20 minutes to obtain a polymer product.

The obtained polymer product was dissolved in ion-exchanged water, and then the resultant aqueous solution was added dropwise to a 20-fold weight of acetonitrile. The resultant precipitate was filtrated and dissolved in ion-exchanged water. Then, the resultant aqueous solution was again added dropwise to a 20-fold weight of acetonitrile. The produced precipitate was filtrated, and heated and dried under vacuum for one day and night at 50° C. to obtain a polymer. When measured by SEC (condition A), the polymer had a weight average molecular weight of $4.0 \times 10^5$.

EXAMPLE IV-8

Copolymerization of Vinyl Sulfonic Acid and Acrylamide by UV Irradiation

A copolymer was obtained by carrying out polymerization in the same manner as in Example IV-7, except that the weights of the vinyl sulfonic acid and the acrylamide were changed to the values shown in Table 10.

EXAMPLE IV-9

Copolymerization of Vinyl Sulfonic Acid and Acrylamide by UV Irradiation

A copolymer was obtained by carrying out polymerization in the same manner as in Example IV-7, except that the weights of the vinyl sulfonic acid and the acrylamide were changed to the values shown in Table 10.

Table 10 shows the weight and mole % of the monomers used in Examples IV-7 to IV-9, and the weight average molecular weights of the obtained copolymers.

TABLE 10

|  | Monomer Composition | | | | Copolymer |
| --- | --- | --- | --- | --- | --- |
|  | Weight (g) | | Mole % | | Weight |
|  | Vinyl Sulfonic Acid | Acrylamide | Vinyl Sulfonic Acid | Acrylamide | Average Molecular Weight |
| Example IV-7 | 0.50 | 0.50 | 40% | 60% | $4.0 \times 10^5$ |
| Example IV-8 | 0.67 | 0.33 | 57% | 43% | $5.6 \times 10^5$ |
| Example IV-9 | 0.91 | 0.09 | 87% | 13% | $8.5 \times 10^4$ |

EXAMPLE IV-10

Copolymerization of Vinyl Sulfonic Acid and Acrylonitrile by UV Irradiation

A 55 mm diameter dish was charged with 0.6 g of the vinyl sulfonic acid obtained in Example 11-2, 2.0 g of acrylonitrile, 0.3 g of N,N-dimethylformamide, and 25 mg of azobisisobutyronitrile, and the resultant mixture was uniformly mixed. The acrylonitrile was produced by charging acrylonitrile (reagent, manufactured by Wako Pure Chemical Industries, Ltd.) into a four-neck flask made from Pyrex (registered trademark) glass, adding 0.1 wt. % hydroquinone monomethyl ether based on the acrylonitrile, and carrying out distillation under reduced pressure to purify the product. The N,N-dimethylformamide was produced by charging N,N-dimethylformamide (reagent, manufactured by Wako Pure Chemical Industries, Ltd.) into a four-neck flask made from Pyrex (registered trademark) glass, and carrying out distillation under reduced pressure to purify the product.

The mixture was irradiated with UV-rays for 25 minutes. Subsequently, the obtained polymer product was dissolved in N,N-dimethylformamide, and the resultant solution was added dropwise to a 20-fold weight of ion-exchanged water. The resultant precipitate was filtrated, and heated and dried under vacuum for one day and night at 50° C. to obtain a polymer.

The obtained polymer was a white transparent solid. When measured by SEC (condition B), the obtained polymer product had a weight average molecular weight of $2.0 \times 10^6$.

EXAMPLE IV-11

Copolymerization of Vinyl Sulfonic Acid and Acrylonitrile by UV Irradiation

A copolymer was obtained by carrying out polymerization in the same manner as in Example IV-10, except that the weights of the vinyl sulfonic acid, the acrylonitrile, and the N,N-dimethylformamide were changed to the values shown in Table 11.

EXAMPLE IV-12

Copolymerization of Vinyl Sulfonic Acid and Acrylonitrile by UV Irradiation

A copolymer was obtained by carrying out polymerization in the same manner as in Example IV-10, except that the weights of the vinyl sulfonic acid, the acrylonitrile, and the N,N-dimethylformamide were changed to the values shown in Table 11.

Table 11 shows the weight and mole % of the monomers used in Examples IV-10 to IV-12, and the weight average molecular weights of the obtained copolymers.

TABLE 11

|  | Monomer Composition |  |  |  |  | Copolymer |
|---|---|---|---|---|---|---|
|  | Weight (g) |  | Mole % |  |  | Weight |
|  | Vinyl Sulfonic Acid | Acrylo-nitrile | Vinyl Sulfonic Acid | Acrylo-nitrile | DMF Weight (g) | Average Molecular Weight |
| Example IV-10 | 0.6 | 2.0 | 13% | 87% | 0.3 | $2.0 \times 10^6$ |
| Example IV-11 | 0.5 | 2.0 | 11% | 89% | 0.25 | $1.4 \times 10^6$ |
| Example IV-12 | 0.4 | 2.0 | 9% | 91% | 0.2 | $1.4 \times 10^6$ |

As shown in Tables 8 to 11, it can be seen that the vinyl sulfonic acid copolymer products having a sufficient weight average molecular weight were obtained using the vinyl sulfonic acid according to the present invention.

EXAMPLE IV-13

Copolymerization of Vinyl Sulfonic Acid and Acrylonitrile by UV Irradiation

A 10 mm quartz cell was charged with 0.9 g of the vinyl sulfonic acid obtained in Example II-4, 1.0 g of acrylonitrile, and 0.45 g of N,N-dimethylformamide, and the resultant mixture was uniformly mixed. The mixture was then irradiated with UV-rays for 40 minutes to obtain a polymer product. The acrylonitrile was produced by charging acrylonitrile (reagent, manufactured by Tokyo Chemical Industry Co., Ltd.) into a four-neck flask made from Pyrex (registered trademark) glass, and carrying out distillation under reduced pressure to purify the product. The N,N-dimethylformamide was produced by charging N,N-dimethylformamide (reagent, manufactured by Wako Pure Chemical Industries, Ltd.) into a four-neck flask made from Pyrex (registered trademark) glass, and carrying out distillation under reduced pressure to purify the product.

The obtained polymer product was dissolved in N,N-dimethylformamide, and then the resultant solution was added dropwise to a 20-fold weight of isopropyl alcohol. The resultant precipitate was filtered, and washed with 100 mL of isopropyl alcohol, and then heated and dried under vacuum for one day and night at 50° C. to obtain 0.19 g of a polymer.

When measured by SEC (condition B), the obtained polymer product had a weight average molecular weight of $3.8 \times 10^6$. Further, the ratio of the vinyl sulfonic acid units in the polymer was measured by subjecting the polymer to ion-exchange with sodium chloride and then titrating with aqueous sodium hydroxide. The measurement value was 13.8 wt. %.

From the results of Example IV-13, it was found that the acrylonitrile copolymer product obtained using the vinyl sulfonic acid having a high purity and a low metal content was a polymer which comprised a large amount of vinyl sulfonic acid units and which had a high molecular weight.

The polymer comprised a large amount of vinyl sulfonic acid units, therefore it is thought that a polymer electrolyte membrane having excellent proton conductivity can be obtained by use of the polymer.

Further, it is thought that a vinyl sulfonic acid copolymer having a high molecular weight has good film-forming properties and can be used to produce a strong membrane.

TEST EXAMPLE 4

Using the vinyl sulfonic acid obtained in Example II-2, a Q value and an e value were determined.

Here, the Q value and the e value are constants represented by the Alfrey-Price formula. These values can be obtained by hypothesizing that a rate constant $k_{12}$ of the following growth reaction, $$M_1 \cdot + M_2 \rightarrow M_2.$$

is represented as follows.

$$k_{12} = P_1 Q_2 \exp(-e_1 e_2)$$

In the formula, $P_1$ represents the level of general reactivity (resonance stabilization) of $M_1 \cdot$, $Q_2$ represents the level of resonance stabilization of $M_2$, $e_1$ and $e_2$ represent the polar effects of $M_1 \cdot$, and $M_2$, respectively.

Styrene was selected as a standard. The Q value of styrene is 1.0, and the e value is −0.8.

A copolymer of the vinyl sulfonic acid obtained in Example II-2 and styrene was produced. The Q value of the obtained vinyl sulfonic acid was 0.09 and the e value was 1.3.

The vinyl sulfonic acid of Non-Patent Document 2 (ethylene sulfonic acid) is described as having a Q value of 0.09 and an e value of 1.3.

Using those values, based on the following formula, the reactivity ratios $r_1$ and $r_2$ with the various copolymer monomers were determined.

$$r_1 = \frac{k_{11}}{k_{12}} = \frac{Q_1}{Q_2} \exp\{-e_1(e_1 - e_2)\}$$
$$r_2 = \frac{k_{22}}{k_{21}} = \frac{Q_2}{Q_1} \exp\{-e_2(e_2 - e_1)\}$$ [Formula 3]

In the formula, $Q_1$ and $e_1$ represent the Q value and the e value of the vinyl sulfonic acid serving as $M_1$. Further, $Q_2$ and $e_2$ represent the Q value and the e value of the various copolymer monomers serving as $M_2$. The values shown in the following tables, which are taken from Polymer Handbook, Fourth Edition (published by John Wiley & Sons Inc., p. II-318-319), were used for the Q value and the e value of the copolymer monomers.

TABLE 12

|  | Q Value | e Value |
|---|---|---|
| Methyl Methacrylate | 0.78 | 0.4 |
| Acrylic Acid | 0.83 | 0.88 |

TABLE 12-continued

|  | Q Value | e Value |
|---|---|---|
| Acrylamide | 0.23 | 0.54 |
| Acrylonitrile | 0.48 | 1.23 |

The Q value and the e value of the vinyl sulfonic acid according to the present invention and that described in Non-Patent Document 2 are shown in Table 13. Further, the obtained reactivity ratios $r_1$ and $r_2$ are also shown in Table 13.

TABLE 13

|  | Non-Patent Document 2 | | Present Invention | |
|---|---|---|---|---|
| M1 | Q Value | e Value | Q Value | e Value |
| Vinyl Sulfonic Acid | 0.09 | 1.3 | 0.12 | 0.9 |
| M2 | $r_1$ | $r_2$ | $r_1$ | $r_2$ |
| Methyl Methacrylate | 0.036 | 12.422 | 0.098 | 7.939 |
| Acrylic Acid | 0.063 | 13.346 | 0.142 | 7.039 |
| Acrylamide | 0.146 | 3.852 | 0.377 | 2.328 |
| Acrylonitrile | 0.171 | 5.813 | 0.336 | 2.666 |

The results show that when the vinyl sulfonic acid according to the present invention was used, $r_1$ increased by a factor of 1.9 to 2.7, so that it can be presumed that a large amount of vinyl sulfonic acid was incorporated in the copolymer.

Consequently, this suggests that copolymer efficiency with various vinyl monomers can be dramatically improved by using the vinyl sulfonic acid according to the present invention. It is thus considered that a copolymer having an increased vinyl sulfonic acid content can be obtained.

If the vinyl sulfonic acid content increases, it is believed that the sulfonic acid group content in the polymer also increases, and that proton conductivity improves. Therefore, it is considered that the copolymer according to the present invention can serve as an excellent polymer electrolyte membrane for a fuel cell.

In addition, by obtaining the vinyl sulfonic acid polymer according to the present invention using a vinyl sulfonic acid having a low metal content, the metal content is also decreased. Therefore, it is considered that the oxidation resistance of the polymer electrolyte membrane is also improved.

The invention claimed is:

1. A vinyl sulfonic acid composition comprising:
   (i) vinyl sulfonic acid;
   (ii) sodium (Na) at a concentration of 1 ppm or less and more than 0 ppm; and
   (iii) at least one metal selected from the group consisting of alkali earth metal and first row transition metal at a concentration of 1 ppm or less and more than 0 ppm;
   wherein the vinyl sulfonic acid composition has a double bond content of 95 wt % or more.

2. The vinyl sulfonic acid composition according to claim 1, wherein
   the concentration of the Na in the vinyl sulfonic acid composition is 100 ppb or less; and
   the concentration of the at least one metal selected from the group consisting of alkali earth metal and first row transition metal in the vinyl sulfonic acid composition is 100 ppb or less.

3. A vinyl sulfonic acid homopolymer or copolymer obtained by polymerizing the vinyl sulfonic acid composition according to claim 1 or 2 alone or with one or more other monomers copolymerizable therewith.

4. A method of producing a vinyl sulfonic acid homopolymer or copolymer, comprising a step of subjecting the vinyl sulfonic acid composition according to claim 1 or 2 alone or with one or more other monomers copolymerizable therewith to radical polymerization, photopolymerization, or radiation polymerization.

5. A method for producing the vinyl sulfonic acid composition according to claim 1, comprising:
   subjecting a vinyl sulfonate to a metal removal treatment; and
   purifying the product obtained from the metal removal treatment using a thin-film distillation apparatus, whose all or a part of vinyl sulfonic acid contact region is formed from a material having a corrosion resistance.

6. The method according to claim 5, wherein the thin-film distillation apparatus comprises:
   a distillation tower for evaporating a distillation raw material;
   a vinyl sulfonic acid vapor outlet which is provided in a middle section of the distillation tower; and
   a cooling device which is arranged externally to the distillation tower for condensing the vinyl sulfonic acid vapor obtained from the outlet.

7. An electric/electronic material comprising the vinyl sulfonic acid composition according to claim 1.

8. An electric/electronic material comprising the vinyl sulfonic acid homopolymer or copolymer according to claim 3.

9. A polymer electrolyte membrane for a fuel cell comprising the vinyl sulfonic acid homopolymer or copolymer according to claim 3.

10. A photoresist composition comprising the vinyl sulfonic acid composition according to claim 1.

11. A conductive polymer composition comprising the vinyl sulfonic acid homopolymer or copolymer according to claim 3 as a dopant.

12. A photoresist composition comprising the vinyl sulfonic acid homopolymer or copolymer according to claim 3.

13. The vinyl sulfonic acid composition according to claim 1 or 2, obtained by a process comprising:
   subjecting a vinyl sulfonate to a metal removal treatment; and
   purifying the product obtained from the metal removal treatment using a thin-film distillation apparatus.

14. The vinyl sulfonic acid composition according to claim 1, wherein the concentration of the Na in the vinyl sulfonic acid composition is from 10 ppb to 1 ppm.

15. The vinyl sulfonic acid composition according to claim 1, wherein the concentration of the at least one metal in the vinyl sulfonic acid composition is from 22.5 ppb to 1 ppm.

16. The vinyl sulfonic acid composition according to claim 1, wherein the vinyl sulfonic acid composition has a double bond content of 99 wt % or more.

17. The method according to claim 5, wherein the material having a corrosion resistance comprises tantalum.

* * * * *